(12) United States Patent
Shen et al.

(10) Patent No.: US 10,252,264 B2
(45) Date of Patent: Apr. 9, 2019

(54) SAMPLE PREPARATION MODULE WITH STEPWISE PRESSURIZATION MECHANISM

(71) Applicant: SLIPCHIP CORPORATION, Chicago, IL (US)

(72) Inventors: Feng Shen, San Jose, CA (US); Chris Da Costa, Vista, CA (US); Hedia Maamar, San Jose, CA (US)

(73) Assignee: Talis Biomedical Corporation, Menlo Park, CA (US)

( * ) Notice: Subject to any disclaimer, the term of this patent is extended or adjusted under 35 U.S.C. 154(b) by 0 days.

(21) Appl. No.: 15/117,156

(22) PCT Filed: Feb. 5, 2015

(86) PCT No.: PCT/US2015/014676
§ 371 (c)(1),
(2) Date: Aug. 5, 2016

(87) PCT Pub. No.: WO2015/160419
PCT Pub. Date: Oct. 22, 2015

(65) Prior Publication Data
US 2016/0346781 A1    Dec. 1, 2016

Related U.S. Application Data

(60) Provisional application No. 61/936,275, filed on Feb. 5, 2014.

(51) Int. Cl.
*B01L 3/00* (2006.01)
*C12N 15/10* (2006.01)
(Continued)

(52) U.S. Cl.
CPC ......... *B01L 3/502715* (2013.01); *B01L 3/502* (2013.01); *C12N 15/1006* (2013.01);
(Continued)

(58) Field of Classification Search
CPC .............. B01L 3/502715; B01L 3/502; C12N 15/1006; G01N 1/405
(Continued)

(56) References Cited

U.S. PATENT DOCUMENTS 4,266,681 A *  5/1981  Fredericks .............. A61J 1/065
                                                            215/47
5,804,141 A     9/1998  Chianese
(Continued)

FOREIGN PATENT DOCUMENTS

EP    2 633 911 A1    9/2013
JP    2011524313      9/2011
(Continued)

OTHER PUBLICATIONS

European Patent Office, Extended European Search Report and Opinion, EP Patent Application No. 14867907.9, dated Apr. 28, 2017, eight pages.
(Continued)

*Primary Examiner* — Jill A Warden
*Assistant Examiner* — Jacqueline Brazin
(74) *Attorney, Agent, or Firm* — Fenwick & West LLP

(57) ABSTRACT

The present invention relates to fluidic systems for controlling one or more fluids or reagents. These systems can be used in combination with one or more devices for assaying, processing, or storing samples. In particular, the systems and related methods can allow for controlled pressure and actuation of fluids.

31 Claims, 19 Drawing Sheets

(51) Int. Cl.
*G01N 1/40* (2006.01)
*G01N 35/00* (2006.01)

(52) U.S. Cl.
CPC ...... *G01N 1/405* (2013.01); *B01L 2200/0621* (2013.01); *B01L 2200/0631* (2013.01); *B01L 2300/021* (2013.01); *B01L 2300/023* (2013.01); *B01L 2300/027* (2013.01); *B01L 2300/0663* (2013.01); *B01L 2300/0681* (2013.01); *B01L 2300/087* (2013.01); *B01L 2300/0832* (2013.01); *B01L 2400/0475* (2013.01); *B01L 2400/0478* (2013.01); *B01L 2400/0487* (2013.01); *B01L 2400/0644* (2013.01); *G01N 2035/00881* (2013.01)

(58) Field of Classification Search
USPC .......................................................... 422/527
See application file for complete search history.

(56) References Cited

U.S. PATENT DOCUMENTS

| | | | |
|---|---|---|---|
| 6,319,476 B1 * | 11/2001 | Victor, Jr. ................. | F15C 5/00 210/198.2 |
| 7,122,153 B2 | 10/2006 | Ho | |
| 2004/0132218 A1 | 7/2004 | Ho | |
| 2006/0216212 A1 | 9/2006 | Lum et al. | |
| 2008/0125704 A1 | 5/2008 | Anderson | |
| 2008/0217246 A1 | 9/2008 | Benn et al. | |
| 2009/0253566 A1 * | 10/2009 | Chavarria ............. | B01L 3/5021 494/43 |
| 2010/0012989 A1 | 1/2010 | Lee et al. | |
| 2010/0129898 A1 | 5/2010 | Squirrell | |
| 2010/0331522 A1 * | 12/2010 | Irvine ...................... | C07H 1/06 530/344 |
| 2011/0244466 A1 | 10/2011 | Juncosa et al. | |
| 2012/0028342 A1 | 2/2012 | Ismagilov et al. | |
| 2012/0107811 A1 | 5/2012 | Kelso et al. | |
| 2013/0280725 A1 | 10/2013 | Ismagilov et al. | |
| 2013/0309679 A1 * | 11/2013 | Ismagilov .......... | C12N 15/1003 435/6.12 |
| 2013/0331298 A1 | 12/2013 | Rea | |
| 2014/0045275 A1 | 2/2014 | Rothacher et al. | |

FOREIGN PATENT DOCUMENTS

| | | |
|---|---|---|
| JP | 2012521219 | 9/2012 |
| JP | 2015514997 | 5/2015 |
| WO | WO 2007/016692 A1 | 2/2007 |
| WO | WO 2012/110159 A1 | 8/2012 |

OTHER PUBLICATIONS

Singapore Invitation to Respond to Written Opinion, Singapore Application No. 11201602064S, dated May 19, 2017, one page.
Singapore Written Opinion, Singapore Application No. 11201602064S, dated May 19, 2017, nine pages.
PCT International Search Report and Written Opinion, International Application No. PCT/US2015/014676, dated Oct. 7, 2015, 15 Pages.
European Patent Office, Extended European Search Report and Opinion, European Patent Application No. EP 15780401.4, dated Aug. 28, 2017, 9 pages.
Communication Pursuant to Article 94(3) EPC for European Patent Application No. EP 15780401.4, dated Apr. 3, 2018, 4 Pages.
Examination Report No. 1 for Australian Patent Application No. 2014357716 dated Jan. 16, 2018, 3 Pages.

* cited by examiner

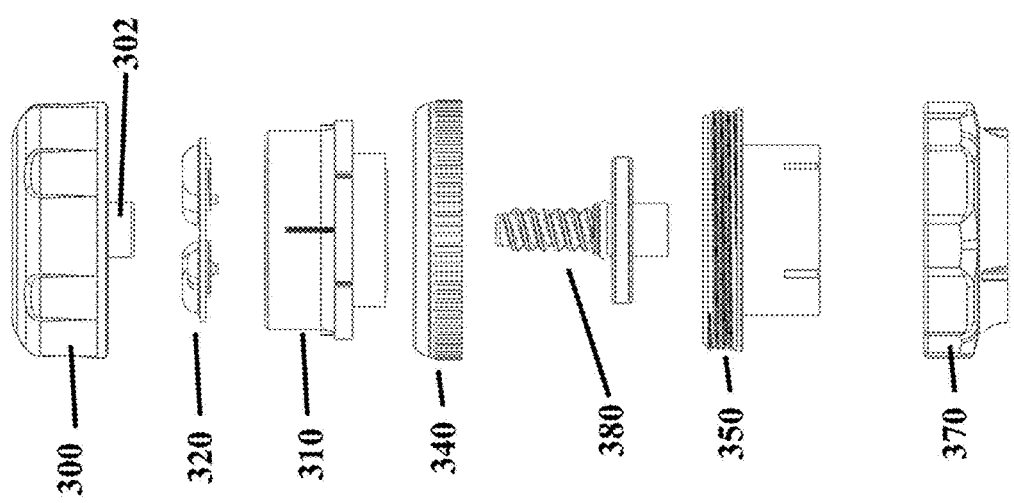

SAMPLE PREPARATION MODULE WITH STEPWISE PRESSURIZATION MECHANISM

CROSS-REFERENCE

This application is the National Stage of International Application No. PCT/US2015/014676, filed Feb. 5, 2015, which claims the benefit of U.S. Provisional Application No. 61/936,275, filed Feb. 5, 2014, all of which applications are incorporated herein by reference.

STATEMENT AS TO FEDERALLY SPONSORED RESEARCH

This invention was made with government support under contract number HR0011-11-2-0006 awarded by the Defense Advanced Research Projects Agency. The government has certain rights in the invention.

BACKGROUND

Modern biological techniques, including nucleic acid analysis, offer powerful tools for the analysis of samples. Samples from subjects and environmental sources can be analyzed for the presence of various compounds and organisms. Patients can be diagnosed for diseases, including infectious diseases and genetic diseases.

However, many analysis techniques require centralized laboratory facilities, trained technicians, sample preparation, refrigeration, and other resources. Such requirements can limit the utility of these techniques in point-of-care settings, limited resource settings, and other environments with difficult or no access to necessary resources.

SUMMARY

What is needed, therefore, is a simple, inexpensive, robust method for nucleic acid based diagnostics at the point of care with immediate availability of results while the health care providers are still with the patient. In addition, a method and device are needed that can provide accuracy results and methodological adherence to proper analytic techniques, as well as quality control measures, particularly those that will permit waiver under the Clinical Laboratory Improvement Amendments (CLIA) program.

Disclosed herein are devices and systems for creating and one or more disrupting fluid paths and for generating pressure using a single mechanical movement. The pressure can serve as a motive force for transferring solution(s) from/to different locations in the device or system. When driving multiple solutions, the movement can simultaneously connect a first fluid path(s) and generate pressure for fluidic transfer; then another movement can disconnect the first fluid path, connect a second fluid path and generate additional pressure for fluidic transfer.

One aspect of the invention provides sample preparation modules comprising a housing having an interior surface, a central shaft comprising a threaded section, wherein the central shaft rotates relative to the housing, a pressure cap and a plurality of coaxially arranged layers, at least one layer being a rotor and one being a stator (relative to the rotor). The pressure cap comprises a gasket capable of engaging with the interior surface of the housing to create an airtight seal and a central column having threads, wherein the threads engage the treaded threaded section of the central shaft. The coaxially arranged layers have complementary facing surfaces assembled in a frictional, sealed engagement, each layer having at least one substantially axially aligned passageway with an upstream entry and a downstream outlet capable for successive selective placement in communication to establish plural dedicated flow paths within the assembly. Rotation of said rotor selectively connects passageways of different coaxially layers thereby serially forming and disrupting a plurality of fluid paths. Additionally, a first coaxially arranged layer engages with the interior surface of the housing to create an airtight seal, the surface of the first layer with the housing and pressure cap thereby forming a compartment, wherein rotation of the shaft relative to the housing compresses the compartment thereby generating pressure against the upstream surface of the first coaxially arranged layer.

In certain implementations, the rotor is engaged directly or indirectly with the shaft and the stator is engaged directly or indirectly with the housing. In other implementations, the stator is engaged directly or indirectly with the shaft and the rotor is engaged directly or indirectly with the housing.

In some implementations, the central shaft engages with a drive. In such implementations, the coaxially arranged layer most proximal to the drive can be partially or fully transparent.

In selected implementations, the pressure cap further comprises a key or keyseat that engages with a complementary keyseat or key in the housing thereby inhibiting rotation of the pressure cap relative to the housing. The pressure cap can further comprise a manual grip.

The threads of the central column can have a different pitch than the threaded section of the shaft. In certain implementations, threaded section of the central shaft is externally threaded and the central column of the pressure cap is internally threaded. In other implementations, the threaded section of the central shaft is internally threaded and the central column of the pressure cap is externally threaded.

In selected implementations, the central shaft comprises a plurality of linked sections, each section engaged with adjacent sections.

The housing can be permanently affixed to a coaxially arranged layer. In various implementations, the housing is comprised of two or more segments that when assembled form airtight junctions. Some, all or none of the two or more segments of the housing can be permanently affixed to a coaxially arranged layer.

In many implementations, the coaxially arranged layers comprise a reagent layer, a separation layer, and a receiving layer. The reagent layer can receive a sample in a first fluid path that is open to the upstream and downstream surfaces. The reagent layer can comprise a second fluid path that is open to the upstream and downstream surfaces. In some implementations, the separation layer comprises a capture separation material occluding the at least one passageway between the upstream and downstream surfaces, said separation material capable of reversibly binding a molecule of interest. Such a sample preparation module can further comprise an analytic layer. The analytic layer can comprise a microfluidic device. In certain implementations, at least one coaxially arranged layer comprises a waste chamber, said waste chamber being a dead end path open only to the upstream surface of the layer. The waste chamber preferably contains an absorbent for waste liquids.

The sample preparation module of the invention can further comprise a re-sealable sample inlet.

Another aspect of the invention provides methods of isolating an analyte of interest from a sample, the method comprising: a) providing a device comprising a pressure cap, a central shaft, and a plurality of coaxially arranged layers, including a reagent layer, a separation layer and a receiving layer, wherein the reagent layer is loaded with a lysis solution, a wash solution and an elution solution, each solution occupying a separate passageway having an upstream entry and downstream outlet, and wherein each of the downstream outlets of the passageways is occluded in a first position of the device; b) combining a sample with the lysis solution in the reagent layer to form a lysed mixture; c) rotating the central shaft to a second position; d) rotating the central shaft to a third position; and e) rotating the central shaft to a fourth position. The step of rotating the central shaft to a second position: 1) rotates the reagent layer relative to the separation layer to align the outlet of the passageway holding the lysed mixture with the upstream entry of a passageway in the separation layer, said passageway in the separation layer being occluded by a capture separation material capable of binding the analyte of interest; and 2) moves the pressure cap toward the plurality of coaxially arranged layers, thereby applying positive pressure to the lysed mixture and forcing the lysed mixture onto and through the capture separation material. The step of rotating the central shaft to a third position: 1) rotates the reagent layer relative to the separation layer to align the outlet of the passageway holding the wash solution with the upstream entry of the passageway in the separation layer occluded by the capture separation material; and 2) moves the pressure cap further toward the plurality of coaxially arranged layers, thereby applying additional positive pressure to force the wash solution through the capture separation material. The step of rotating the central shaft to a fourth position: 1) rotates the reagent layer relative to the separation layer to align the outlet of the passageway holding the elution solution with the upstream entry of the passageway in the separation layer occluded by the capture separation material; 2) rotates the separation layer relative to the receiving layer to align the outlet of the passageway occluded with the capture separation material with the upstream entry of a first passageway in the receiving layer; and 3) moves the pressure cap yet further toward the plurality of coaxially arranged layers, thereby applying additional positive pressure to force the elution solution through the capture separation material to detach the analyte of interest from the capture separation material and collect the elution solution and analyte of interest in the passageway of the receiving layer.

In certain implementations, the analyte of interest is a molecule. In some implementations, the analyte of interest is a particle. In certain implementations, the analyte of interest is a cell. In some implementations, the analyte of interest is a spore.

Another aspect of the invention provides methods of isolating a molecule of interest from a sample, the method comprising: a) providing a device comprising a pressure cap, a central shaft, and a plurality of coaxially arranged layers, including a reagent layer, a separation layer and a receiving layer; b) loading the reagent layer with a lysis solution, wash solution and elution solution, each solution occupying a separate passageway having an upstream entry and downstream outlet, wherein each of the downstream outlets of the passageways is occluded in a first position of the device; c) combining a sample with the lysis solution in the reagent layer to form a lysed mixture; d) rotating the central shaft to a second position; e) rotating the central shaft to a third position; and f) rotating the central shaft to a fourth position. The step of rotating the central shaft to a second position: 1) rotates the reagent layer relative to the separation layer to align the outlet of the passageway holding the lysed mixture with the upstream entry of a passageway in the separation layer, said passageway in the separation layer being occluded by a capture separation material capable of binding the molecule of interest; and 2) moves the pressure cap toward the plurality of coaxially arranged layers, thereby applying positive pressure to the lysed mixture and forcing the lysed mixture onto and through the capture separation material. The step of rotating the central shaft to a third position: 1) rotates the reagent layer relative to the separation layer to align the outlet of the passageway holding the wash solution with the upstream entry of the passageway in the separation layer occluded by the capture separation material; and 2) moves the pressure cap further toward the plurality of coaxially arranged layers, thereby applying additional positive pressure to force the wash solution through the capture separation material. The step of rotating the central shaft to a fourth position: 1) rotates the reagent layer relative to the separation layer to align the outlet of the passageway holding the elution solution with the upstream entry of the passageway in the separation layer occluded by the capture separation material; 2) rotates the separation layer relative to the receiving layer to align the outlet of the passageway occluded with the capture separation material with the upstream entry of a first passageway in the receiving layer; and 3) moves the pressure cap yet further toward the plurality of coaxially arranged layers, thereby applying additional positive pressure to force the elution solution through the capture separation material to detach the molecule of interest from the capture separation material and collect the elution solution and molecule of interest in the passageway of the receiving layer.

In certain implementations, rotating the central shaft to the second position further comprises rotating the separation layer relative to the receiving layer to align the outlet of the passageway occluded with the capture separation material with the upstream entry of a second passageway in the receiving layer, said second passageway configured to capture waste liquids. Preferably, the waste liquids are captured in an absorbent housed in the second passageway of the receiving layer.

In some implementations, the plurality of coaxially arranged layers includes an analytic layer and the method further comprise the step of g) rotating the central shaft to a fifth position, thereby 1) rotating the receiving layer relative to the analytic layer to align the outlet of the passageway holding the elution solution and molecule of interest with the upstream entry of a passageway in the analytic layer; and 2) moving the pressure cap further toward the plurality of coaxially arranged layers, thereby applying additional positive pressure to force the elution solution and molecule of interest into the passageway of the analytic layer. In selected implementations, the molecule of interest is a nucleic acid and the analytic layer is configured to amplify the nucleic acid.

In many implementations, the molecule of interest is a nucleic acid or a protein, more preferably a nucleic acid. The nucleic acid can be RNA and/or DNA.

Yet another aspect of the invention provides devices for simultaneously modifying fluid paths and generating pressure, said device comprising a pressure cap; and a plurality of coaxially arranged layers, at least one being a rotor and at least one being a stator, said coaxially arranged layers having complementary facing surfaces assembled in a frictional, sealed engagement, each layer having at least one substantially axially aligned passageway with an upstream entry and a downstream outlet capable for successive selective placement in communication to establish plural dedicated flow paths within the assembly, wherein a first coaxially arranged layer engages with the pressure cap to create an airtight compartment that is compressible upon rotation of the rotor, and wherein rotation of said rotor selectively connects passageways of different coaxially layers thereby serially forming and disrupting a plurality of fluid paths.

The invention also features a kit including one or more devices and/or systems described herein and a collector (e.g., for collecting a sample for use with the device or system, such as any described herein, including a lancet, a capillary, a needle, a syringe, a swab, a sample tube, collection cup or a microtube). In further embodiments, the kit further includes one or more substances either separate from the device or within the device. Exemplary substances include any described herein, including one or more of a sample, a lysis solution, a washing solution, an elution solution, a reagent, a dye, a desiccant, a stabilizer, a protein, a nucleic acid, a filter, a membrane, a marker, and/or a container.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows an exemplary exploded side view schematic of a pressure cap device.

DETAILED DESCRIPTION OF THE INVENTION

Definitions

Figure 1:
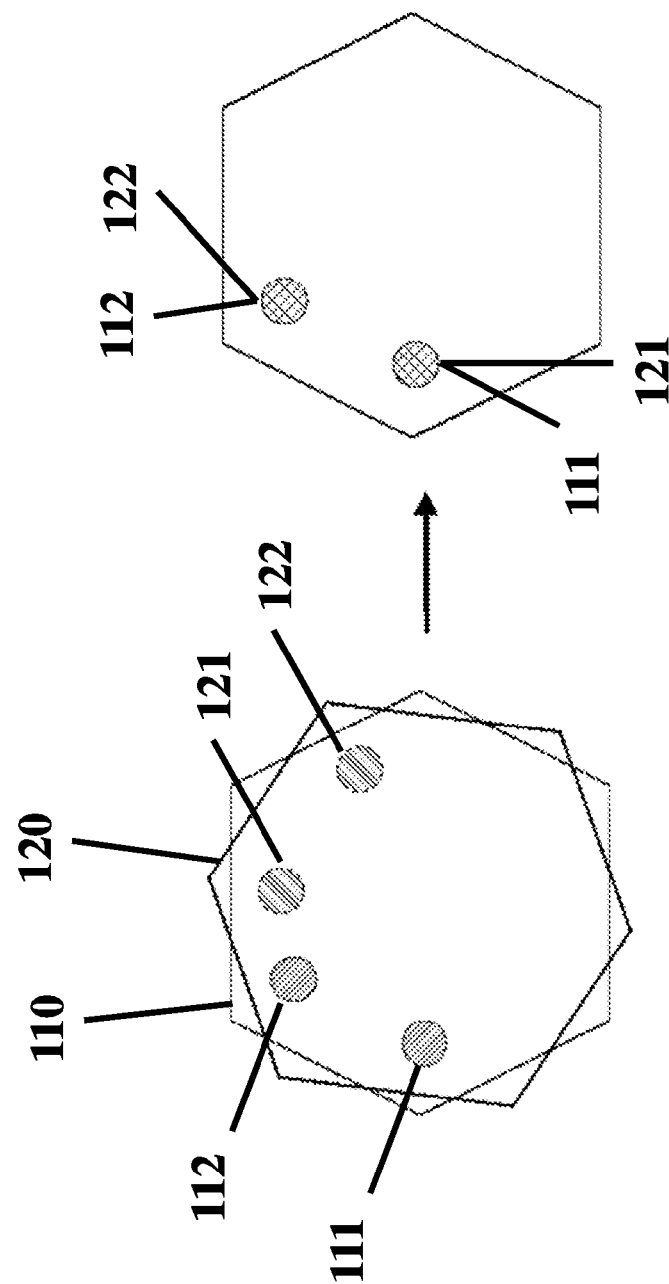
FIG. 1 shows an exemplary schematic of the alignment of two layers of a device.

As used herein, "about" means +/−10% of the recited value.

As used herein, "or" includes "and/or."

By "between" is meant a relative position in which an intermediate structure separates a first and a second structure. For instance, in a device including an intermediate substrate disposed between a first and a second substrate, the term "between" provides the relative positional relationship of the first, second, and intermediate substrates and in no way signifies that the first substrate must necessarily be the top or uppermost substrate in the device.

By "engage" is meant a physical interaction between two components or structures. This physical interaction can be direct (e.g., where a first component interacts with a second component) or indirect (e.g., where a first component interacts with an interleaving component, which in turn interacts with a second component).

As used herein the terms "upstream" and "downstream" are defined relative to the direction of positive pressure, such as that created by a pressure cap.

Devices

Disclosed herein are devices and systems for creating and disrupting fluid paths and for generating pressure using a single movement. The pressure can serve as a motive force for transferring solution(s) or other fluid(s) from/to different locations in the device or system. When driving multiple solutions, the movement can simultaneously connect a first fluid path(s) and generate pressure for fluidic transfer; then another movement can disconnect the first fluid path, connect a second fluid path and generate additional pressure for fluidic transfer.

One implementation provides devices for simultaneously modifying fluid paths and generating pressure, said device comprising a pressure cap and a plurality of coaxially arranged layers, at least one being a rotor and at least one being a stator, said coaxially arranged layers having complementary facing surfaces assembled in a frictional, sealed engagement, each layer having at least one passageway with an upstream entry and a downstream outlet capable for successive selective placement in communication to establish plural dedicated flow paths within the assembly, wherein a first coaxially arranged layer engages with the pressure cap to create an airtight compartment that is compressible upon rotation of the rotor, and wherein rotation of said rotor selectively connects passageways of different coaxially layers thereby serially forming and disrupting a plurality of fluid paths.

Another implementation provides devices comprising a housing having an interior surface, a central shaft comprising a threaded section, wherein the central shaft rotates relative to the housing, a pressure cap, and a plurality of coaxially arranged layers.

Preferably the pressure cap comprises a gasket capable of engaging with the interior surface of the housing to create an airtight seal and a central column having threads, wherein the threads engage the treaded section of the shaft. The first coaxially arranged layer can engage with the interior surface of the housing to create an airtight seal, the surface of the first layer with the housing and pressure cap thereby forming a compartment, wherein rotation of the central shaft relative to the housing compresses the compartment thereby generating pressure against the upstream surface of the first coaxially arranged layer.

At least one of the plurality of coaxially arranged layers is a rotor. One or more of the remaining layers is a stator (relative to the rotor). The rotor(s) can be engaged directly or indirectly with the central shaft, whereas the stator(s) can be engaged directly or indirectly with the housing. In certain implementations, the stator is permanently affixed to the housing, thus acting effectively as a base for the housing. Alternatively, the stator(s) can be engaged directly or indirectly with the central shaft, whereas the rotor(s) can be engaged directly or indirectly with the housing. Thus, when the central shaft and housing rotated relative to one another, the rotor(s) and stator(s) also rotate relative to one another. The coaxially arranged layers have complementary facing surfaces and are assembled in a frictional, sealed engagement, each layer having at least one passageway with an upstream entry and a downstream outlet capable for successive selective placement in communication to establish plural dedicated flow paths within the assembly. During operation rotation of said rotor selectively connects passageways of different coaxially layers thereby serially forming and disrupting a plurality of fluid paths.

The devices of the invention can include layers arranged (e.g., coaxially) to allow for connection and disconnection of one or more fluid paths by movement of the layers (e.g., rotational movement). For example, in a first position, one or more passageways (e.g., 111, 112) in a first layer (e.g., 110) are not connected to (e.g., are not in fluidic communication with) one or more passageways (e.g., 121, 122) in a second layer (e.g., 120). Upon moving the first layer relative to the second layer, the downstream outlets of one or more passageways of the first layer align with the entries of the one or more passageways of the second layer and a connection is formed (see, e.g., FIG. 1). This movement can be accomplished by rotating the first layer having the first passageway relative to the second layer. Alternatively, this movement can include rotating the second layer having the second passageway relative to the first layer.

When configured for manual rotation, a device can comprise one or more grooves, flats, stops, steps, markers, or other features designed to guide the rotation to desired position(s). For example, the layers with the module can comprise one or more straight edges on their exterior edges to encourage alignment of multiple layers (see, e.g., FIG. 1)

Rotation of a device can be performed manually (e.g., by the hand of one or more users). In some cases, rotation is assisted by fixing the device (e.g., the base of the device) to a support (e.g., a surface such as a desk or bench top). The device can include one or more features to aid with manual gripping, such as ridges, tabs, handles, grooves, or knobs (see e.g. FIG. 3, more particularly the grip 373 for the base and depressions in the cap). In some cases, gripping features are present on both the top and the base of the device to aid in manual rotation. In other implementations, the features are present on a ring between the top and base of the device.

Rotation of a device can be performed with the aid of a source of mechanical force, such as a motor, a spring (e.g., a linear spring, a spiral spring, a torsional spring, a constant force spring), or an elastic band. Sources of mechanical force, such as motors, can be driven by power supplies. Examples of power supplies include but are not limited to batteries, solar panels, connectors or adaptors for wall or grid power, connectors or adaptors for motor vehicle power (e.g., 12 volt adaptor), hand cranks, and capacitors. When using a mechanical force, e.g. contained within a base station, the device can comprise one or more flanges, knobs, slots or other structures adapted to engage with a non-rotating portion of the base station to keep certain portions of the device stationary, thus allowing different parts of the device to rotate relative to one another. One example of such a flange 371 is provided in FIG. 3.

Devices can contain fluidic elements or structures, such as channels, reservoirs, chambers, blister packs, wells, filters, membranes, one-way valves, and sample tubes. The dimensions of any structure (e.g., one or more channels) may be chosen to maintain a particular volumetric or linear flow rate of a fluid in the device. For example, choice of such dimensions can be useful to control the filling of the device with particular fluids or the flow rate of such fluids through pathways, filters and/or wells or aeration to effect mixing of liquids.

The wells, channels, reservoirs, chambers, tubes or other structure can include any useful cross-section. Cross-sections can be of any useful shape (e.g., rectangular, square, circular, oval, trapezoidal, triangular, or irregular cross-sections). Cross-section shape or dimensions can vary along the axis of any structure. For instance, when the structure is a channel, the cross-section of the channel along the axis of fluid flow can change from one cross-sectional shape to another, such as from a circular to a rectangular cross-section. In another instance, the dimensions of the cross-section can be uniform or can vary along any axis, such as a channel that tapers or expands along the axis of fluid flow.

The housing, shaft, coaxially arranged layers, and pressure cap can be formed from any useful material or combination of materials. The materials used to form the components of devices of the invention are selected with regard to physical and chemical characteristics that are desirable for proper functioning of the component. Suitable, non-limiting examples of materials include plastics (e.g., cyclic olefin copolymer (COC), cyclic olefin polymer (COP), polyethylene terephthalate (PET), polyethylene (PE), high-density polyethylene (HDPE), low-density polyethylene (LDPE), polyvinyl chloride (PVC), polypropylene (PP), polystyrene (PS), high impact polystyrene (HIPS), polyamides (PA), acrylonitrile butadiene styrene (ABS), polyethylene/acrylonitrile butadiene styrene (PE/ABS), polycarbonate (PC), polycarbonate/acrylonitrile butadiene styrene (PC/ABS), polymethylmethacrylate (PMMA)), metals, elastomers (e.g., polydimethylsiloxane (PDMS)), glass (e.g., borosilicate), ceramics, and composite materials, such as carbon fiber composites. In some cases, devices are formed from metal or other magnetic materials.

The device or components thereof can be formed by any useful process, including but not limited to molding (e.g., injection molding, vacuum molding, or over-molding), machining (e.g., drilling, milling, or sanding), embossing (e.g., hot embossing) and etching (e.g., laser, deep reactive ion etching, KOH etching, or HF etching). In microfluidic applications, the layers can be fabricated from a material that enables formation of high resolution features such as microchannels, chambers, mixing features, and the like, that are of millimeter, micron, or submicron dimensions (e.g., PDMS, PMMA, glass). Applicable microfabrication techniques include but are not limited to dry etching, wet etching, laser etching, laser ablation, molding, embossing, photolithography, soft lithography, lamination or the like.

Pressure Cap

Figure 2:
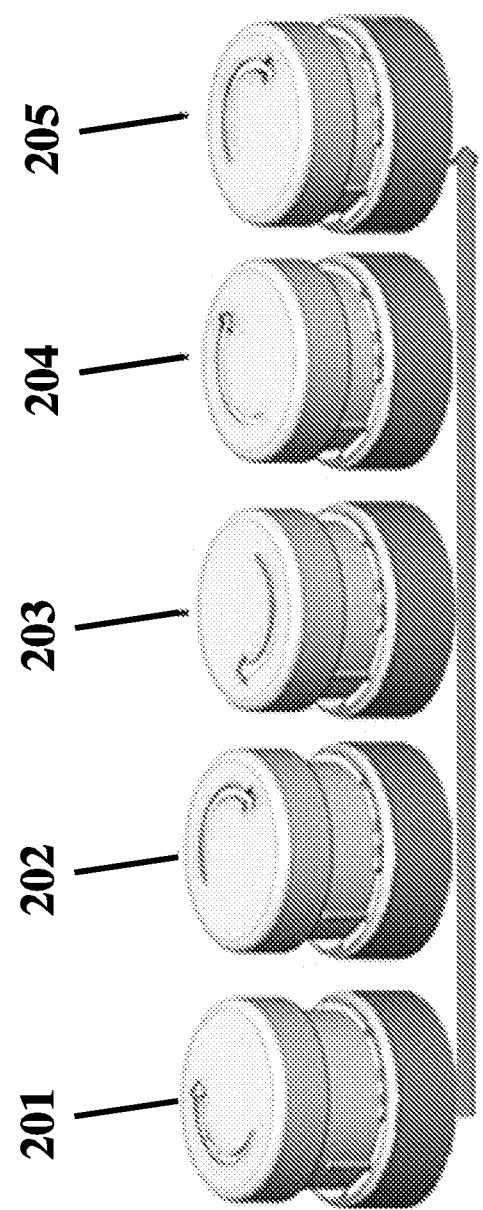
FIG. 2 shows an exemplary schematic of a device with a pressure cap being rotated, thereby compressing the air compartment to generate pressure.
Figure 3B:
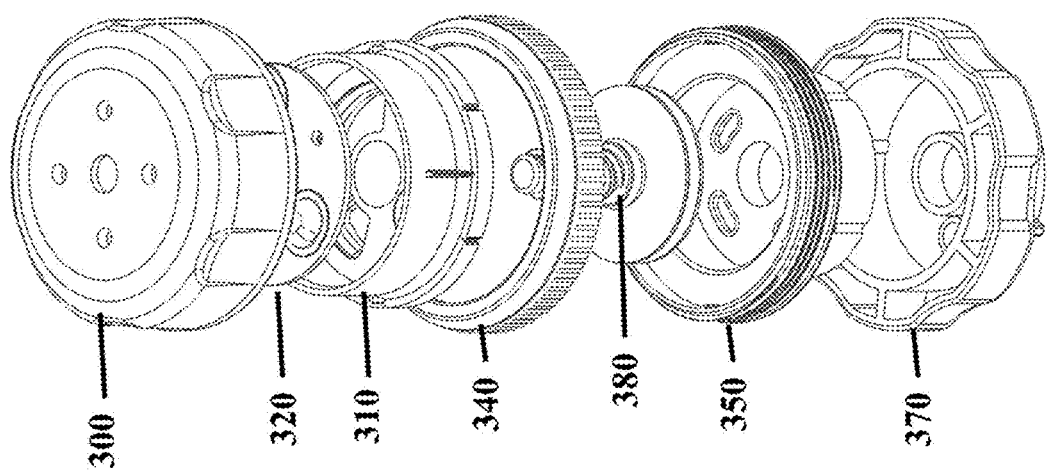
FIG. 3B shows an exemplary exploded three-quarters view schematic of a device comprising a pressure cap and plurality of coaxially arranged layers.
Figure 3C:
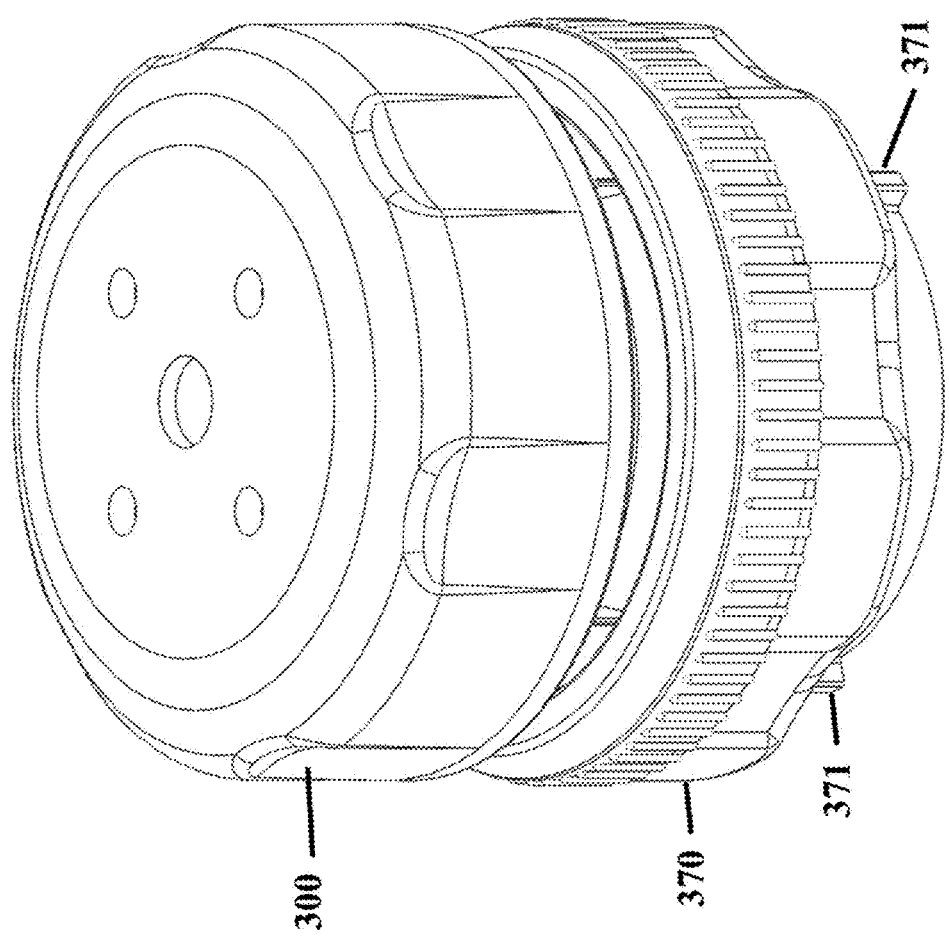
FIG. 3C shows an exemplary three-quarters upper view schematic of a device comprising a pressure cap and plurality of coaxially arranged layers.
Figure 3D:
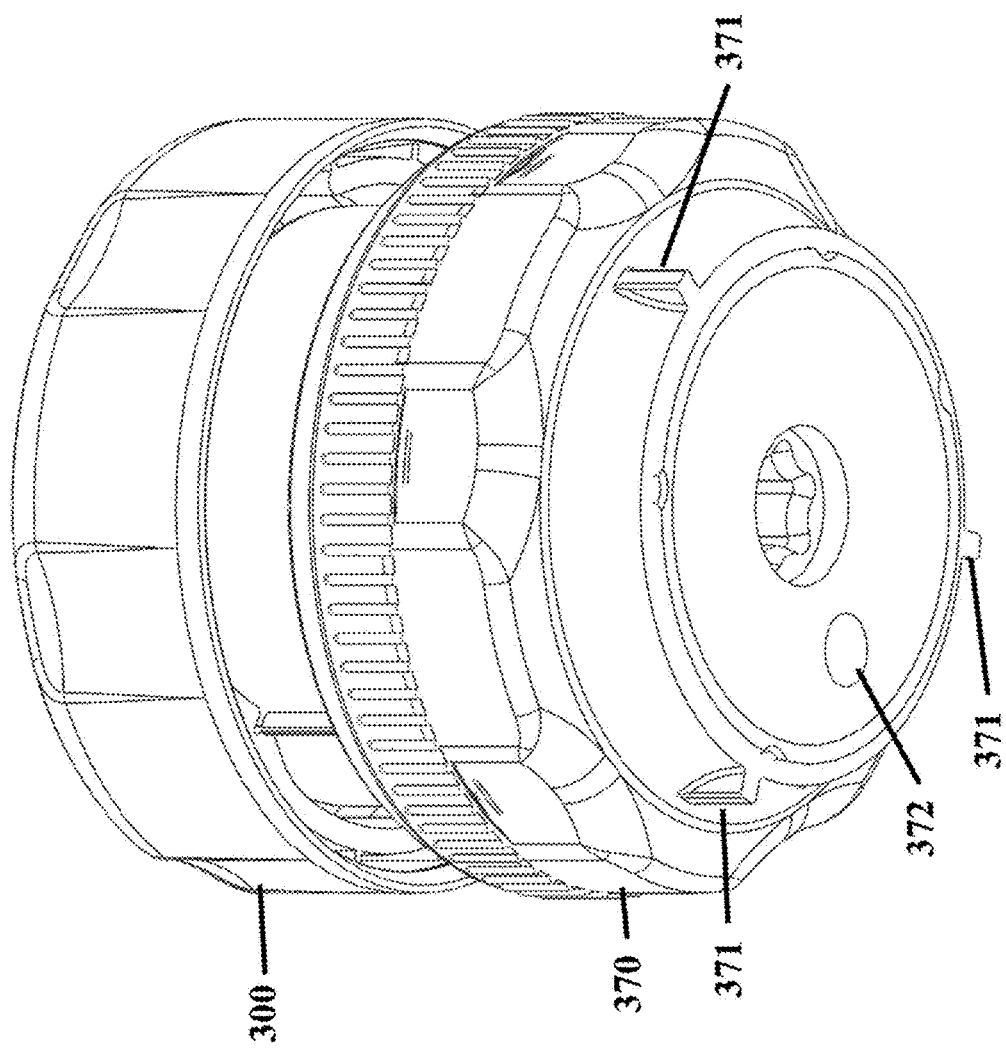
FIG. 3D shows an exemplary three-quarters lower view schematic of a device comprising a pressure cap and plurality of coaxially arranged layers.
Figure 3E:
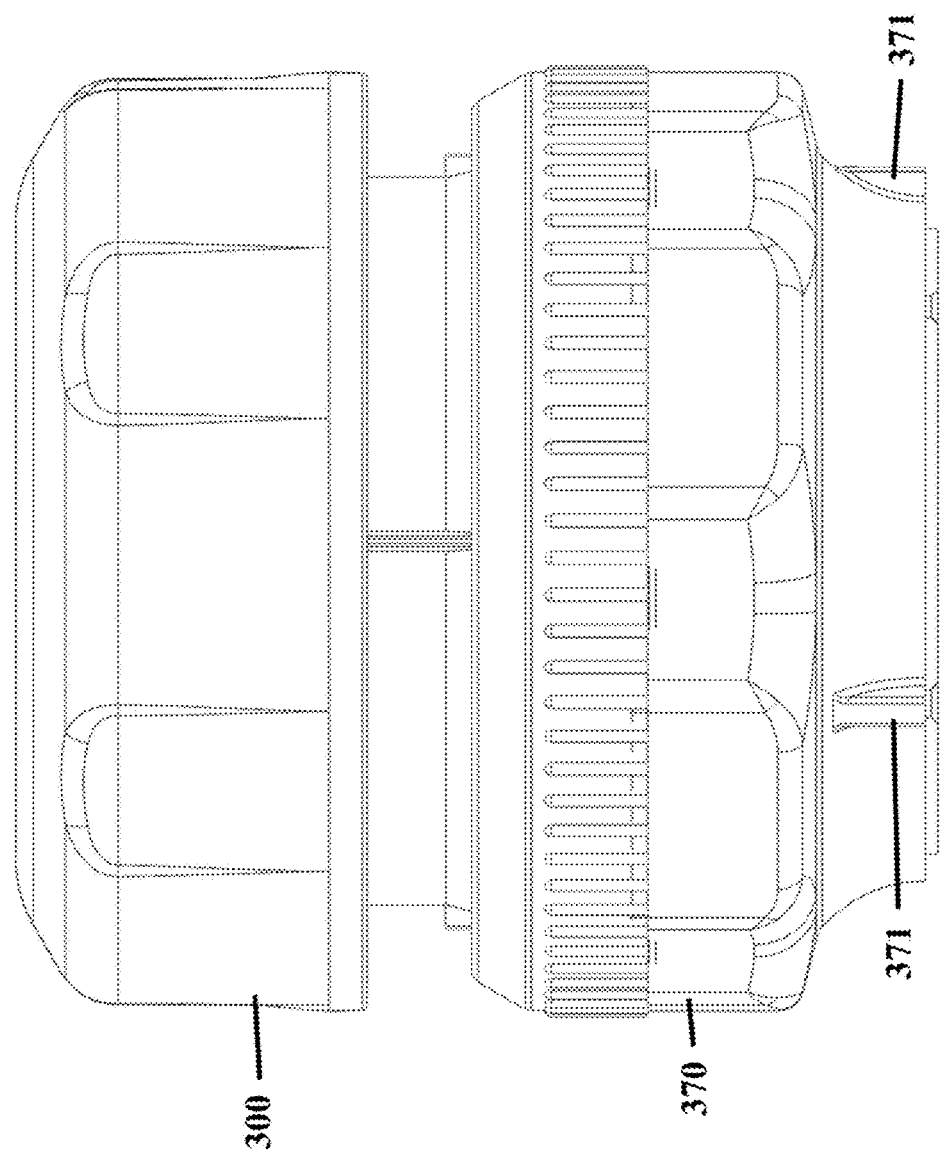
FIG. 3E shows an exemplary side view schematic of a device comprising a pressure cap and plurality of coaxially arranged layers.
Figure 4:
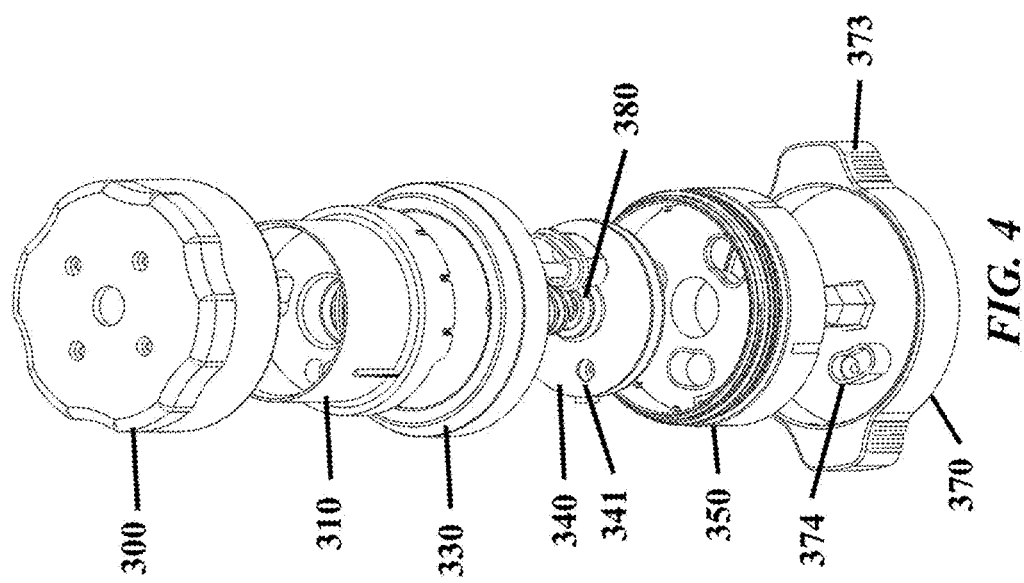
FIG. 4 shows an exemplary exploded three-quarters view schematic of a 200 µL device configured with a heating well.

A rotational device can be configured to increase pressure within the device as the cap is rotated. For example, FIG. 2 shows a cap designed to add additional pressure by each rotation step (e.g., 201, 202, 203, 204, and 205). This pressure can be generated by the decreasing internal volume of a compartment within the device as the cap lowers toward the base. In some examples, such a device comprises a center shaft (e.g., 380, FIG. 3A-3E) with a thread, allowing a central column on the cap to thread onto the central shaft and screw down with rotation. In other examples, an outer part of the housing or base can comprise threads onto which the cap can thread and screw down with rotation. In some cases, one or more posts, knobs, grooves, guiderails, or other features can guide the motion of the cap. In one implementation, the pressure cap comprises a key or keyseat that engages with a complementary keyseat or key in the housing thereby inhibiting rotation of the pressure cap relative to the housing. The motion of the cap can be characterized by a smooth motion of combined rotation and downward motion relative to the base. In other examples, the motion of the cap can be characterized by variable rate motion, e.g. a first 15° rotation resulting a quarter-inch downward motion of the cap and a second 15° rotation resulting in a half-inch downward motion of the cap.

The housing can be formed as a single structure or can be comprised of two or more segments that, when assembled, form an airtight unit. In some implementations, the housing is permanently affixed to the first (i.e. most upstream) layer of the device. The permanent fixation can be achieved by forming the housing and first layer from a single material, e.g., co-molded in plastic. Alternatively, the housing and first layer can be permanently attached using any adhesive, preferably air and fluid resistant, known in the art. In those implementations in which the housing is formed of two or more segments, one or more of those segments can be permanently affixed to a coaxially arranged layer. In certain implementations, each of the two or more segments of the housing are permanently affixed to a coaxially arranged layer.

Pressure generated by the cap can be used to drive fluid flow within the device. For example, solution can be impelled through a matrix or filter, or air can be driven to dry a matrix or filter. The graduated application of pressure produced by a smooth motion of the cap can reduce the risk of leakage compared to a sudden application of pressure.

The cap can generate pressures of at least about 1 kilopascal (kPa), 2 kPa, 3 kPa, 4 kPa, 5 kPa, 6 kPa, 7 kPa, 8 kPa, 9 kPa, 10 kPa, 15 kPa, 20 kPa, 25 kPa, 30 kPa, 35 kPa, 40 kPa, 45 kPa, 50 kPa, 55 kPa, 60 kPa, 65 kPa, 70 kPa, 75 kPa, 80 kPa, 85 kPa, 90 kPa, 95 kPa, 100 kPa, 110 kPa, 120 kPa, 130 kPa, 140 kPa, 150 kPa, 160 kPa, 170 kPa, 180 kPa, 190 kPa, 200 kPa, 210 kPa, 220 kPa, 230 kPa, 240 kPa, 250 kPa, 260 kPa, 270 kPa, 280 kPa, 290 kPa, 300 kPa, 310 kPa, 320 kPa, 330 kPa, 340 kPa, 350 kPa, 360 kPa, 370 kPa, 380 kPa, 390 kPa, 400 kPa, 410 kPa, 420 kPa, 430 kPa, 440 kPa, 450 kPa, 460 kPa, 470 kPa, 480 kPa, 490 kPa, or 500 kPa.

The cap can generate a number of distinct pressures (e.g., for particular fluid operations or steps), including 1, 2, 3, 4, 5, 6, 7, 8, 9, 10, 11, 12, 13, 14, 15, 16, 17, 18, 19, 20, 25, or more distinct pressures.

In some cases, actuation of the device can create a vacuum or negative pressure in one region of the device relative to the rest of the device. For example, actuation of the device can cause actuation of piston to drop down and create a reduced or negative pressure, such as in a passageway or below a filter. Alternatively, the direction of rotation can be reversed, thereby expanding the compartment formed by the pressure cap and thus creating a negative pressure. Such negative pressure can be used to pause or reverse fluid flows. In certain implementations, the direction of rotation can be alternated between clockwise and counter-clockwise to generate a back and forth flow to, e.g. mix solutions or dissolve a solid reagent deposited in a passageway. In another implementation, the actuation of the device can cause shape change of a buckle pump or diaphragm. Locally different pressures can be achieved in different sections of the device through the use of one-way or check valves.

Layers

FIG. 3A-3E, FIG. 4, FIG. 5, FIG. 6, and FIG. 7 show exemplary schematics of a device with a pressure cap and various layers. Device components can include but are not limited to a pressure cap 300, a central column 302, a gasket 304, a housing 310, a reagent layer 320, a reagent layer storage 330, a separation layer 340, a receiving layer 350, a central threaded shaft 380, an analysis layer 360, a base 370, and a threaded connector 390 adapted to hold other components in place. Not all of these components are required to be present in a particular device. One or more of the layers can include heating, such as the reagent storage layer and/or the receiving layer. Layers can fulfill multiple functions; for example, a layer can comprise a membrane to serve as a separation layer and also comprise a well to serve as a receiving layer. Additionally, a single structure can comprise both a layer and additional structures, such as a housing or shaft. In a preferred implementation, the device comprises reagent layer, a separation layer and a receiving layer.

General Layer Characteristics

Each layer can have similar or different geometry compared to the other layers. A layer can be round, can have a plurality of straight edges, or can comprise a combination of arcs and straight edges.

Each layer can comprise at least one complete fluid passageway through the layer. Each layer can comprise one or more dead end paths that have an entry on the upstream side, but do not pass through the layer (e.g., a well). Wells can be used for applications such as holding waste products (e.g., lysed cell debris below filter, wash fluid) or receiving processed product material (e.g., purified nucleic acids).

Leakage between layers can be mitigated or prevented by methods including but not limited to the use of seals (e.g., elastomeric materials), sealing fluids (e.g., fluids immiscible with the fluids being flowed through the device), grease, soft waxes, and lubrication (e.g., dry lubricants, wet lubricants). For example, one or more layers can comprise an elastomeric material useful for creating a seal with adjacent layers.

In order to improve layer's sealing with adjacent layers, in some implementations, a deformable layer can be attached to both the top and bottom surfaces of the layer. Examples of deformable layer materials include but are not limited to silicone, polysiloxanes, polyurethane, rubber, chlorosulfonated polyethylene synthetic rubber, neoprene nylon, expanded polytetrafluoroethylene (PTFE), nitrile butadiene rubber (NBR), neoprene, nitrile nylon, and polydimethylsiloxanes. In an exemplary implementation, the deformable layer is silicone. The silicone, or other appropriate material, can deform under pressure and match the shape of the structures, e.g. entries and/or outlets, on the adjacent layers of the device, thus sealably engaging the present layer with adjacent layers. When a deformable layer is attached to the surface of a layer, sealing can be further enhanced by providing slightly raised ridges on the adjacent layer's surface. Preferably such ridges define an enclosed shape, typically surrounding an opening in that layer's surface. While such ridges can be any shape or height that would enhance sealing to the adjacent layer, the ridges can be about 0.05 µm, 0.075 µm, 0.1 µm, 0.11 µm, 0.12 µm, 0.13 µm, 0.14 µm, 0.15 µm. Inclusion of such raised ridges does not alter the complementary character of the surface of the layer.

Any layer in the device described herein can comprise one or more heating elements for altering or maintaining the temperature of fluid in one or more passageways through or wells in that layer. Said heating element can comprise, for example, Peltier elements or resistive heaters located in or adjacent to the layer. In other implementations, a foil heater can be wrapped around a passageway, such as a lysis well, to heat solution(s) contained therein. In other implementations, a heater can be placed inside the passageway.

After pressurization and forcing the sample into or through a particular passageway, excess air pressure can be released by allowing air to pass through one or more passageways. In this manner, an air flush can be used to remove dead volume in a matrix, chamber, conduit or other structure. In some embodiments, such an air flush can dry separation material in a separation layer. In some implementations, pressure within the device increases with each rotation providing additional force to move solutions through later-formed fluid paths.

In certain implementations, one or more layers are permanently affixed to other structures of the device. For example a layer engaged with the central shaft can be permanently affixed to (e.g. co-molded with) the threaded central shaft. See, for example, the separation layer 340 and central shaft 380 of FIG. 3. Similarly, a layer engaged with the housing can be permanently affixed to the housing. See, for example, the housing 310 and reagent layer 320 of FIG. 3. In other implementations, one or more layers can engage with the central shaft or housing in a detachable manner. For example, the layer can engage with one or more posts, knobs, keys/keyseats, grooves, gear teeth, slots, guiderails, or other features on the shaft or housing.

Wells, chambers, reagent packs, and other regions can be characterized by a volume. Such regions can have the same volume, or different regions can have different volumes. The volume of a well, chamber, reagent pack, or other region can be at least about 1 nanoliter (nL), 2 nL, 5 nL, 10 nL, 20 nL, 30 nL, 40 nL, 50 nL, 60 nL, 70 nL, 80 nL, 90 nL, 100 nL, 150 nL, 200 nL, 250 nL, 300 nL, 350 nL, 400 nL, 450 nL, 500 nL, 600 nL, 700 nL, 800 nL, 900 nL, 1 microliter (µL), 2 µL, 5 µL, 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 15 mL, 20 mL, 25 mL, 30 mL, 35 mL, 40 mL, 45 mL, or 50 mL. The volume of a well, chamber, reagent pack, or other region can be at most about 1 nanoliter (nL), 2 nL, 5 nL, 10 nL, 20 nL, 30 nL, 40 nL, 50 nL, 60 nL, 70 nL, 80 nL, 90 nL, 100 nL, 150 nL, 200 nL, 250 nL, 300 nL, 350 nL, 400 nL, 450 nL, 500 nL, 600 nL, 700 nL, 800 nL, 900 nL, 1 microliter (µL), 2 µL, 5 µL, 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 15 mL, 20 mL, 25 mL, 30 mL, 35 mL, 40 mL, 45 mL, or 50 mL. The volume of a well, chamber, reagent pack, or other region can be about 1 nanoliter (nL), 2 nL, 5 nL, 10 nL, 20 nL, 30 nL, 40 nL, 50 nL, 60 nL, 70 nL, 80 nL, 90 nL, 100 nL, 150 nL, 200 nL, 250 nL, 300 nL, 350 nL, 400 nL, 450 nL, 500 nL, 600 nL, 700 nL, 800 nL, 900 nL, 1 microliter (µL), 2 µL, 5 µL, 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 15 mL, 20 mL, 25 mL, 30 mL, 35 mL, 40 mL, 45 mL, or 50 mL.

Passageways

Layers can comprise one or more passageways. A passageway can be a channel, conduit, chamber, or other structure in which at least one complete path traverses the layer. The passageways can include any useful cross-section or plurality of cross-sections along their paths. Cross-sections can be of any useful shape (e.g., rectangular, square, circular, oval, trapezoidal, triangular, or irregular cross-sections). Cross-section shape or dimensions can vary along the axis of any structure. For instance, the cross-section of the passageway along the axis of fluid flow can change from one cross-sectional shape or area to another, such as from a circular to a rectangular cross-section. In another instance, the dimensions of the cross-section can be uniform or can vary along any axis, such as a passageway that tapers or expands along the axis of fluid flow.

Similarly, the path of any passageway can be linear, twisting, curved, serpentine, or any other track shape. Twisting or serpentine paths may be selected to encourage mixing of components of a fluid. The passageways can additionally contain columns, posts, dimples, humps, weirs, hydrophobic patches, hydrophilic patches, or other structures to improve mixing of fluids as they pass. Implementations in which the passageway is linear can achieve rapid transfer of a fluid under minimal pressure. The passageway can be substantially axially aligned, with the upstream opening being directly or nearly directly above the downstream opening. Alternatively, the upstream and downstream opening can be offset by any distance.

A passageway or channel can have a cross-sectional area of at least about 1, 2, 5, 10, 20, 50, 100, 200, 500, 1000, 2000, 5000, 10000, 20000, 50000, or 100,000 square micrometers, or 1, 10, 20, 30, 40, 50, 60, 70, 80, 90, 100, 200, 300, 400, 500, 600, 700, 800, 900 or 1000 square millimeters. A passage or channel can have a cross-sectional area of at most about 1, 2, 5, 10, 20, 50, 100, 200, 500, 1000, 2000, 5000, 10000, 20000, 50000, or 100,000 square micrometers or 1, 2, 3, 4, 5, 6, 7, 8, 9, 10, 20, 30, 40, 50, 60, 70, 80, 90, or 100 square millimeters. A passage or channel can have a cross-sectional area of about 1, 2, 5, 10, 20, 50, 100, 200, 500, 1000, 2000, 5000, 10000, 20000, 50000, or 100,000 square micrometers or 1, 2, 3, 4, 5, 6, 7, 8, 9, 10, 20, 30, 40, 50, 60, 70, 80, 90, or 100 square millimeters.

For passageways, the size, length, cross-sectional area, other geometric factors, or any combination thereof can be selected to control flow rates, pressures, or other characteristics of fluid flow through the passageway.

Layers can comprise additional passageways for pressure balance or equalization rather than liquid handling. Such passageways can be distributed around the edge or circumference of the layer. For example, FIG. 8A-8D shows a layer with five passageways: a lysis chamber 321, a wash chamber 322, an elution chamber 323, and two pressure balance passageways 324, 325. Inclusion of one or more pressure balance passageways can prevent or mitigate pinching of one side of a device relative to the other, which could lead to gapping or leakage.

Each layer can include at least one passageway that opens to both the upstream and downstream surfaces of the layer. Additionally, the openings can encompass channels or apertures arranged on the surface that form conduits and/or chambers when mated to adjacent layer(s). These channels can be formed by a variety of means, such as by being molded or cut into the layers. Alternatively, the openings in the surfaces can be defined by a gasket material between the layers.

Reagent Layer

The device described herein can comprise one or more reagent layers. The reagent layer can comprise one or more conduits or chambers capable of holding liquid or solid reagents for use during sample preparation. Reagents conduits or chambers can comprise simple chambers formed in the device layer, blister packs, or other containers.

The device can comprise a blister pack layer. Such a blister pack can comprise blisters of a variety of sizes, for example from 1 µL to 10 mL. While any method known in the art can be utilized, preferably blisters are formed using heat-sealing, adhesive, pressure sealing, or other sealing mechanisms. In certain implementations, the layer comprising the blister pack has a piercing structure under the blister, and further the layer contains one or more passageways to dispense solution from blister to designed area after piecing. The piercing structure can be fabricated from metal, plastic, glass, or ceramics. Pressure built up with the device can be applied on the blister to cause shape deformation, and piercing structure can break the bottle seal of the blister, and solution can be dispensed through the fluidic path. Alternatively, the device can comprise a mechanism for physically breaking the blisters, such as a cam or posts projecting from an adjacent layer.

In some cases, the reagent layer includes a passageway adapted for receiving a sample and lysing cells, i.e. a lysis chamber. The lysis chamber may have any suitable shape and configuration, but typically will be in the form of a well or chamber of sufficient volume to receive and process a clinically relevant sample. The lysis chamber may be adapted for lyses of eukaryotic or prokaryotic cells as well as disruption of certain particles in a fluid sample.

In one implementation, the reagent layer receives the sample in a first fluid path that is open to the upstream and downstream surfaces. The reagent layer can comprise a second fluid path that is open to the upstream and downstream surfaces In certain examples, the device comprises a plurality of reagent storage layers. For example, the module can comprise a first reagent storage layer holding reagents related to nucleic acid isolation and a second reagent storage layer holding reagents related to nucleic acid amplification. In such an example, the first reagent storage layer would typically be placed upstream of a separation layer and the second reagent storage layer would be placed downstream of the separation layer.

In certain implementations, the reagent layer can comprise a passageway arranged as a fragmentation unit. In some methods, random fragmentation of DNA or RNA can be desirable, or even necessary, as a sample pre-treatment step. Fragmentation can be achieved biochemically using restriction enzymes, or through application of a physical force to break the molecules. The positive pressure generated by the pressure cap during operation of the devices described herein can be used to fragment nucleic acid as the sample passes through a short constriction (e.g., by shear or other stress). In some implementations, DNA and/or RNA breaks under mechanical force when pushed through a narrow orifice, due to rapid stretching of the molecule. A pressure-driven flow can lead to a shear force, which leads to fragmentation of the nucleic acids.

Reagents can be preloaded on the device. Reagents also can be loaded by a user. In some cases, some reagents are provided preloaded on the device and some (e.g., perishable reagents) are provided by a user prior to operation. Reagents can be provided in wet or dry form. In some examples, the reagent storage layer is preloaded with one or more reagents. In such an example, the reagents can be contained with a membrane configured to be pierced or disrupted during operation of the module. In some examples, the membrane comprises foil, laminate and/or plastic. In other examples, dry reagents are rehydrated by a user prior to use of the device. For example, a user can load water into a device to rehydrate reagents, and then a user can load a sample into the device and operate the device.

Exemplary reagents can include, but are not limited to, lysis solutions, wash solutions, elution solutions, rehydration solutions, enzyme solutions (e.g., nucleic acid amplification enzymes, polymerase enzymes, restriction enzymes), buffers, liquid, powder, pellets, a gel, microbeads, probes, primers, nucleic acids, DNA, RNA, polypeptides, nucleoside triphosphates (NTPs), antibodies, a sacrificial reagent or any combination thereof. A sacrificial reagent can comprise an aqueous solution, a lubricant, an oil, an aqueous-immiscible liquid, a gel, a gas, a fluorocarbon oil, a surfactant, gas, air, or any combination thereof. For example, the air can be used to generate air bubble for mixing. As another example, air and immiscible liquid can be used to remove leftover solution (dead volume) in the matrix. Reagents can be mixed to change their composition. For example, one type of buffer can be mixed with another buffer or a dry reagent to change its composition to another buffer.

A device can include at least 1, 2, 3, 4, 5, 6, 7, 8, 9, 10, 15, 20, 25, 30, 35, 40, 45, 50, or more different reagents. A device can include volumes of reagents including at least about at least about 1 nanoliter (nL), 2 nL, 5 nL, 10 nL, 20 nL, 30 nL, 40 nL, 50 nL, 60 nL, 70 nL, 80 nL, 90 nL, 100 nL, 150 nL, 200 nL, 250 nL, 300 nL, 350 nL, 400 nL, 450 nL, 500 nL, 600 nL, 700 nL, 800 nL, 900 nL, 1 microliter (µL), 2 µL, 5 µL, 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 15 mL, 20 mL, 25 mL, 30 mL, 35 mL, 40 mL, 45 mL, or 50 mL each.

Separation Layer

The device described herein can comprise one or more separation layers. The separation layer can comprise one or more passageways occluded with a separation material 341, said separation material capable of binding an analyte of interest, such as a molecule or cell.

Systems and devices described herein can comprise filters, membranes, gels, and other separation materials, which can be located on a separation layer. The presence of a separation material in a channel, open chamber, or conduit can increase the resistance to flow through that structure. Parameters of a separation material can be chosen to provide a specific resistance to control the operation time and pressure required to pass a sample or reagent into or through the separation material. Parameters of a separation material can include thickness, density, porosity, pore size, wettability or hydrophobicity, binding affinity, or electrical charge of the material. For example, a separation material with greater thickness or smaller pore size can be characterized by a larger resistance to flow and can increase the amount of time or pressure required for a fluid or reagent to dispense from a prior layer. On the other hand, a separation material with lesser thickness or larger pore size can be characterized by a smaller resistance to flow and can decrease the amount of time for a fluid or reagent to dispense from a prior layer.

The separation material can be any useful material for binding one or more molecules of interest. The separation material can be any useful material for binding one or more other analytes of interest (e.g., cells, spores, particles). Exemplary materials includes a filter, a matrix, a polymer, a charge switch material, a gel, and a membrane (e.g., a silica membrane, a glass-fiber, membrane, a cellulose membrane, a nitrocellulose membrane, a polysulfone membrane, a nylon membrane, a polyvinylidene difluoride membrane, a vinyl copolymer membrane, or an ion exchange membrane, including any described herein a fiber (e.g., a glass fiber), or a particle (e.g., a silica particle, a bead, an affinity resin, or an ion exchange resin). In certain implementations, the separation material can comprise a capture moiety. Suitable capture moieties include small organic molecules, such as dyes and tryazines, and biopolymers such as peptides, proteins (including antibodies, and fragments thereof), polynucleotides, oligosaccharides or lipids. Capture moieties of the present invention may be molecules having molecular weights of 100 KDa or more, such as antibodies, but preferably are smaller molecules with a molecular weight in the range of 10 KDa, more preferably around 1 KDa, desirably less than 1 KDa for example, less than 750, 500, or 250 Da. Ideally, capture moieties are coupled to an insoluble particulate or polymeric material. Each insoluble particle preferably carries several copies of the same capture moiety, with each particle type coupling a different capture moiety.

Separation materials, such as membranes or filters, can be characterized by a pore size or an average pore size of at least about 0.1 µm, 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, 5.0 µm, about 10 µm, about 15 µm, about 20 µm, or about 25 µm. In some cases, the pore size or average pore size of a separation material is from about 0.7 µm to about 4.0 µm.

Separation materials can have a thickness of about 0.1 µm, 0.5 µm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 10 mm, or more. Separation materials can have an area of about 1, 2, 5, 10, 20, 50, 100, 200, 500, 1000, 2000, 5000, 10000, 20000, 50000, or 100,000 square micrometers or 1, 2, 3, 4, 5, 6, 7, 8, 9, 10, 20, 30, 40, 50, 60, 70, 80, 90, or 100 square millimeters, or more.

Receiving Layer

A receiving layer can comprise one or more chambers or wells to receive fluids. For example, a receiving layer can comprise one or more product wells to receive a product, such as purified nucleic acids. A receiving layer can comprise one or more waste wells to receive waste fluids, such as wash buffers. A waste well can comprise one or more absorbents. Absorbents can be used to absorb fluids such as waste fluids. Exemplary absorbents include but are not limited to pads, diaper polymers (such as polyacrylic acid variants), powders, particles, pellets, gels, paper, fabric, fibers, capillary and desiccants.

Conduits, chambers, wells, and other structures on a receiving layer can be open- or closed-ended. Open-ended conduits can allow transit of fluids of interest to subsequent layer, such as an analytic layer. At least a portion of the material or substrate defining a passageway, e.g. a conduit, chamber, well, or other structure, can be transparent, translucent, or otherwise compatible with taking measurements of the sample inside (e.g., optical measurements). In some cases, an entire layer can be transparent or translucent. In some implementations, particularly those in which detection is performed by a base station, the layer most proximal to the drive shaft is partially or fully transparent. See, e.g., the viewing window 372 of FIG. 3D.

Chambers or wells in a receiving layer can comprise or connect to outlets allowing the recovery of material. For example, purified nucleic acids can be recovered for subsequent use off-device.

Analytic Layer

The modules, devices and systems described herein can be integrated with other devices to allow multistep processes. For example, the sample preparation modules can be included in a device by exploiting the modularity of Slip-Chip devices, in order to prepare the sample before storage. Examples include but are not limited to devices for multistep protocols for nucleic acid extraction and filtration elements to separate plasma from whole blood using membranes and/or integrated filtration elements such as geometrical features in the device (for example, restrictions or a gap between the layers). In a preferred implementation, the analytic layer comprises a microfluidic device.

An analytic layer can comprise chambers or other features for analysis of a sample, such as by nucleic acid amplification. An analytic layer can comprise reagents for analysis, such as nucleic acid reagents; alternatively, an analytic layer can receive analysis reagents from a reagent layer.

Analysis can indicate the presence, absence, or quantity of an analyte of interest. For example, nucleic acid amplification can provide qualitative or quantitative information about a sample, such as the presence, absence, or abundance of a cell, cell type, pathogen (e.g., bacteria, virus), toxin, pollutant, infectious agent, gene, gene expression product, methylation product, genetic mutation, or biomarker (e.g., nucleic acid, protein, or small molecule).

Analytical targets of interest can include indicators of diseases or illnesses such as genetic diseases, respiratory diseases, cardiovascular diseases, cancers, neurological diseases, autoimmune diseases, pulmonary diseases, reproductive diseases, fetal diseases, Alzheimer's disease, bovine spongiform encephalopathy (Mad Cow disease), *chlamydia*, cholera, cryptosporidiosis, dengue, giardia, gonorrhea, human immunodeficiency virus (HIV), hepatitis (e.g., A, B, or C), herpes (e.g., oral or genital), human papilloma virus (HPV), influenza, Japanese encephalitis, malaria, measles, meningitis, methicillin-resistant *Staphylococcus aureus* (MRSA), Middle East Respiratory Syndrome (MERS), onchocerciasis, pneumonia, rotavirus, schistosomiasis, shigella, strep throat, syphilis, tuberculosis, trichomonas, typhoid, and yellow fever. Analytical targets can include biomarkers indicative of traumatic brain injury, kidney disease, cardiovascular disease, cardiovascular events (e.g., heart attack, stroke), or susceptibility of certain infectious agents (such as bacteria or viruses) to certain therapeutic agents. Analytical targets can include genetic markers, such as polymorphisms (e.g., single nucleotide polymorphisms (SNPs), copy number variations), gene expression products, specific proteins or modifications (e.g. glycosylation or other post-translational processing) of proteins.

Coordinated Motion

Coordinated pressurization and rotation can simplify the operation or manipulation of the device. The device can be driven by a single rotational movement, and the switching of fluidic path and pressurization can be achieved simultaneously. The device can be fully autonomous driven by a single movement powered by springs, motors, or manually. By being coordinated, the present device can provide more reliability than systems requiring a plurality of motive forces, since the failure of any of the plurality of forces would render the device useless.

The motion of the layers can be around a shared motive axis. The motion around the motive axis can be around a central axis. An axis can comprise a single shaft. An axis can comprise multiple linked shafts.

A shaft can comprise threads (e.g., on its external surface) or other structures for engaging with another surface. A shaft can engage with another surface, such as a pressure cap. For example, threads on the external surface of a shaft can engage with threads on the internal surface of a pressure cap sleeve. Threads can extend around the full circumference of the central shaft, or there can be breaks in the threading around the shaft circumference. The surface with which the central shaft engages, such as the pressure cap sleeve, can have threads extending around the full or only a portion of its circumference. In one implementation, the externally threaded section of a shaft is distal to the location of engagement of the central shaft with a drive. In other implementations the pressure cap comprises external threads on cap and the shaft comprises internal threads along at least a portion of the length of the shaft.

Threads can have variable pitch, which can result in a variable compression per degree of rotation of a pressure cap. For example, the thread pitch can change along the length of a shaft, cap, or other surface. Similarly, the pitch of the threads of the cap need not be the same as the pitch of the shaft or other surface with which the cap's threads engage. For example, the threads of the central column of the pressure cap can have a different pitch that the threaded section of the shaft.

In some cases, the shaft comprises a plurality of linked sections, with each section engaged with its neighboring (e.g., proximal or distal) sections to form an arrangement of stacked shafts. Shaft sections can be linked directly, such that each section rotates at the same rate. Shaft sections can be linked via a geared linkage. Geared linkages can enable different rates of rotation between neighboring shaft sections. Rotation between neighboring shaft sections can be characterized by proportional movement, non-proportional movement, or discontinuous movement.

Rotatable layers can be engaged directly with a shaft or shaft section. Rotatable layers can be engaged indirectly with a shaft or shaft section, such as by engagement mediated via another rotatable layer, or by engagement with external threads on a surface such as a pressure cap sleeve. A rotatable layer can be permanently attached to a shaft.

The angular rotation of a layer can be the same as the angular rotation of a shaft (e.g., central shaft). Alternatively, the angular rotation of a layer can be different from the angular rotation of a shaft (e.g., central shaft). Some layers on a shaft can have an angular rotation that is the same as the shaft while other layers have a different angular rotation. Angular rotation between a layer and a shaft can be proportional (e.g. 3:1 or 1:3).

Base Station

The devices of the present disclosure can be used in conjunction with a base station. In some examples, the coaxially arranged layers have minimal or no active mechanical or electronic components. When carrying out an assay, such mechanical or electronic functionality can be provided by manual rotation or by a base station.

Primarily, a base station can engage with the central shaft of a device and provide the motive force and control of rotation. Rotation of a device can be performed with the aid of a source of mechanical force, such as a motor, a spring (e.g., a linear spring, a spiral spring, a torsional spring, a constant force spring), or an elastic band. Sources of mechanical force, such as motors, can be driven by power supplies. Examples of power supplies include but are not limited to batteries, solar panels, connectors or adaptors for wall or grid power, connectors or adaptors for motor vehicle power (e.g., 12 volt adaptor), hand cranks, and capacitors.

The base station may provide additional functions. For example, a base station can have one or more light detectors for measuring luminescence generated. Light detectors that can be used include, but are not limited to photomultiplier tubes, avalanche photodiodes, photodiodes, photodiode arrays, CCD chips, CMOS chips, film. The light detector may be comprised within an optical detection system that also comprise lenses, filters, shutters, apertures, fiber optics, light guides, illumination sources, or other components.

The base station can comprise components, including but not limited to heaters, sensors, detectors, mixing devices (such as acoustic or vibrating mechanisms), barcode or RFID readers, and other components. Components can be used for verifying the presence of fluids. Components can be used for maintaining the fluids at an appropriate controlled temperature. The base station can be used to store and provide assay reagents, either onboard the station itself or from separate assay reagent bottles or an assay reagent storage device. The base station can have a microprocessor for controlling the mechanical and/or electronic subsystems, analyzing the acquired data and/or providing a graphical user interface (GUI). The base station may also comprise electrical, mechanical and/or optical connectors for connecting to the sample preparation device.

Detectors can be present in a device or system (e.g., base station) of the present disclosure. For example, imaging or sensor components can be used to record or measure reactions within a device by techniques including but not limited to optical detection, x-ray detection, absorption spectrometry, matrix-assisted laser desorption/ionization (MALDI), mass spectrometry, Raman spectrometry, fluorescence correlation spectroscopy (FCS), fluorescence polarization/fluorescence correlation spectroscopy (FP/FCS), fluorometric detection, colorimetric detection, chemiluminescence, bioluminescence, scattering, surface plasmon resonance, electrochemical detection, pH sensing, temperature sensing, electrophoresis, lasers, or fluorescent imaging plate reader (e.g., FLIPR®, Molecular Devices) assays.

Sensors or detectors can comprise any solid state image sensor including a charged coupled device (CCD), charge injection device (CID), photo diode array (PDA), or complementary metal oxide semiconductor (CMOS). Sensors or detectors can comprise a photomultiplier tube (PMT).

Sensors can be used for quality control. For example, sensors can indicate if a device has been subjected to conditions that may render it inoperable (e.g., extreme temperature compromising preloaded reagents or stored processed sample). In another example, one or more properties of a sample, waste, or other effluent can be measured and validated against a standard, such as pH.

A device or base station can comprise a timing unit, such as a clock. Timing units can allow for automated control of device operation (e.g., rotation). Timing units can guide a user in manual operation of a device, such as by indicating that a desired amount of time for a wait step has elapsed and that the user can proceed to the next step.

Figure 9:
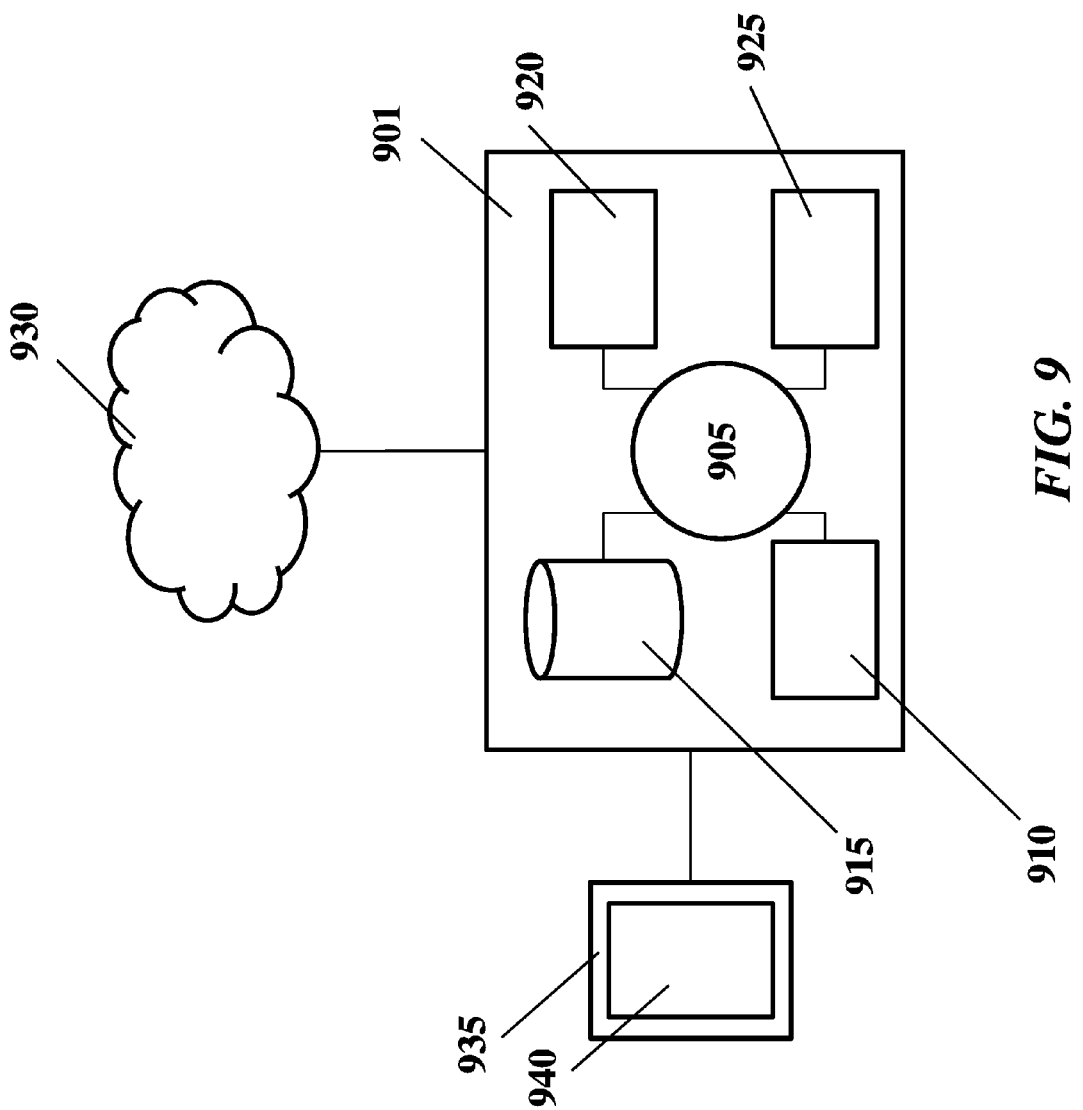
FIG. 9 shows a computer control system that is programmed or otherwise configured to implement methods provided herein.

The present disclosure provides computer control systems that are programmed to implement methods of the disclosure. FIG. 9 shows a computer system 901 that is programmed or otherwise configured to operate a device or analyze results from a device of the present disclosure. The computer system 901 can regulate various aspects of device operation of the present disclosure, such as, for example, device rotation, timing between rotation steps, and on-device reactions. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and write back.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930 (e.g., wired or wireless). For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, timing information or analysis results. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, control on-device temperature, process analysis results, or operate a device.

Sample Handling

In some cases, the device further comprises a sample inlet port or sample input well. Given the pressurization inherent to the devices described herein, the sample inlet preferably is air tight. In certain implementations, the sample inlet is configured to be opened to permit addition of a sample and then resealed after the sample is loaded to the device. Alternatively, the sample can be loaded via a puncturable septa or large one-way valve. The device can include an integrated sample loader, such as a bulb or syringe, useful for loading a sample into the device. The device can be packaged with a sample collection device, such as a syringe, bulb, swab, scraper, biopsy punch, or other tool for a user to collect a sample.

Samples can be obtained from a subject (e.g., human subject), a food sample (e.g., including an organism), or an environmental sample (e.g., including one or more organisms). Exemplary, non-limiting samples include blood, plasma, serum, sputum, urine, fecal matter (e.g., stool sample), swab, sweat, spinal fluid, amniotic fluid, interstitial fluid, tear fluid, bone marrow, tissue sample (e.g., a skin sample or a biopsy sample), a buccal mouthwash sample, an aerosol (e.g., produced by coughing), nucleic acid, cell (e.g., tumor cells, fetal cells in blood, stem cells, bacterial and fungal cells, T-cells, or B-cells), protein, enzyme, soil, water, compost pile, manure pile, sediment (e.g., marine or freshwater sediment), a water sample, an air sample, rock, a plant sample, a food sample, or a gut sample. The sample can include any useful target or analyte to be detected, filtered, concentrated, and/or processed.

In some cases, all of a sample is analyzed within a device. In other cases, some of a sample (e.g., purified nucleic acid) is analyzed within a device and some is reserved for later use. In other cases, all of a sample is reserved for later use. Sample, such as purified nucleic acids, can be stored on the device or can be outlet into a sample container such as a tube or vial. A sample container can be sealed. A sample container can be sterile.

A sample can be marked, numbered, or labeled to identify its source. A mark can comprise a code, such as an alpha-numeric code or an optical barcode on the device or on a sample container. A mark can comprise an electronic mark, such as data or an indicator in an RFID tag or other electronic medium. A mark can comprise unique identifiers mixed in with the sample, such as nucleic acid barcodes or particles, which can be identified later (e.g., by amplification, DNA chip readout, or sequencing). A mark, such as a nucleic acid barcode, can comprise sequencing adaptors (e.g., Illumina adaptors).

Methods

In some aspects, this disclosure provides a method of isolating a biological molecule comprising: (i) providing the module or device or system of aspects or embodiments provided herein; (ii) introducing a sample into the device or system, wherein the sample comprises one or more molecules of interest; (iii) sequentially passing the sample through one or more coaxially arranged layers; and (iv) eluting the one or more biological molecules, thereby obtaining an eluted sample.

One aspect provides methods method of isolating a molecule of interest from a sample, the method comprising: a) providing a device comprising a pressure cap, a central shaft, and a plurality of coaxially arranged layers, including a reagent layer, a separation layer and a receiving layer (see, e.g., FIG. 8A); b) loading the reagent layer with a lysis solution, wash solution and elution solution, each solution occupying a separate passageway having an upstream entry and downstream outlet, wherein each of the downstream outlets of the passageways is occluded in a first position of the device; c) combining a sample with the lysis solution in the reagent layer to form a lysed mixture; d) rotating the central shaft to a second position; e) rotating the central shaft to a third position; and f) rotating the central shaft to a fourth position. Rotating the central shaft to a second position (see, e.g., FIG. 8B): 1) rotates the reagent layer relative to the separation layer to align the outlet of the passageway holding the lysed mixture with the upstream entry of a passageway in the separation layer, said passageway in the separation layer being occluded by a separation material capable of binding the molecule of interest; and 2) moves the pressure cap toward the plurality of coaxially arranged layers, thereby applying positive pressure to the lysed mixture and forcing the lysed mixture onto and through the separation material. Rotating the central shaft to a third position (see, e.g., FIG. 8C): 1) rotates the reagent layer relative to the separation layer to align the outlet of the passageway holding the wash solution with the upstream entry of the passageway in the separation layer occluded by the separation material; and 2) moves the pressure cap further toward the plurality of coaxially arranged layers, thereby applying additional positive pressure to force the wash solution through the separation material. Rotating the central shaft to a fourth position (see, e.g., FIG. 8D): 1) rotates the reagent layer relative to the separation layer to align the outlet of the passageway holding the elution solution with the upstream entry of the passageway in the separation layer occluded by the separation material; 2) rotates the separation layer relative to the receiving layer to align the outlet of the passageway occluded with the separation material with the upstream entry of a first passageway in the receiving layer; and 3) moves the pressure cap further toward the plurality of coaxially arranged layers, thereby applying additional positive pressure to force the elution solution through the separation material to detach the molecule of interest from the separation material and collect the elution solution and molecule of interest in the passageway of the receiving layer.

In some implementations, rotating the central shaft to the second position further comprises rotating the separation layer 340 relative to a receiving layer to align the outlet of the passageway occluded with the capture material with the upstream entry of a second passageway in the receiving layer, said second passageway configured to capture waste liquids. The passageway configured to capture waste liquids can be a dead end path, i.e. a waste well. In certain implementations, the waste liquids are captures in an absorbent housed in the waste well.

In another implementation, the plurality of coaxially arranged layers includes an analytic layer and the method further comprise the step of: g) rotating the central shaft to a fifth position, thereby 1) rotating the receiving layer relative to the analytic layer to align the outlet of the passageway holding the elution solution and molecule of interest with the upstream entry of a passageway in the analytic layer; and 2) moving the pressure cap further toward the plurality of coaxially arranged layers, thereby applying additional positive pressure to force the elution solution and molecule of interest into the passageway of the analytic layer. The analytic layer can be configured to amplify molecule of interest that is a nucleic acid.

In some implementations, reagents or samples can be added partway through the operation (e.g., rotation and pressurization) of a device. In some implementations, a given sample can be passed through or processed in a device multiple times.

EXAMPLES

Example 1: 200 µL Sample Preparation Device

A sample preparation module was designed with a pressurization cap that can provide approximately 6 psi positive pressure with each rotation. A center post with thread pulls the cap down with each rotation, and positive air pressure is generated by compressing the air in the chamber. This positive pressure can drive the solution in the designed well through the separation material and also dry the filter via the passage of air.

The sample preparation module (see, e.g., FIG. 4) was designed to process approximately 200 µL of sample, plus 600 µL lysis reagent, 500 µL of washing buffer, and 50 µL of elution buffer. The large volume of sample allows high-sensitivity detection of target molecules at low concentrations, which both improves the lower detection limit and dynamic range. Eluted nucleic acid was captured in a well 374 on the bottom layer after it passed through the separation material.

The module was further designed to integrate electric temperature control module into the rotational sample preparation device to enable heating of a sample solution to the desired temperature (63±2° C.). The sample well was machined from thermally conductive material, and a foil heater and control thermistor were placed on the outside wall of the well. This well was directly attached on the reagent layer in the rotational sample preparation device. The heating module was controlled by an electronic control unit, and the performance was measured with the thermal probe (Thorlabs), which was placed directly in the well surrounded by the testing solution. The data were recorded by using Thorlabs temperature sensor probe TSP 01 software at an interval of 1 second. The device was evaluated with 800 µL of water using a plug-in power supply at a voltage of 4.58 volts at room temperature. The device was tested three times, and the solution could be heated to the desired temperature (63±2° C.) within 140 seconds, with the standard deviation less than 0.3° C. during the testing period. When repeated using four AA batteries as the power supply at room temperature, the solution could be heated up to the desired temperature within 150 seconds, with the standard deviation less than 0.1° C. during the testing period.

Since the thermal properties of fluid vary, the performance of the heated well has evaluated using 200 µL of human plasma and 600 µL of ZR Viral RNA lysis buffer (Zymo viral RNA kit) with plug-in power supply at a voltage of 4.58 volts at room temperature. The device was tested three times, and the solution could be heated up to the desired temperature within around 180 seconds, with the standard deviation less than 0.3° C. during the testing period. When repeated using four AA batteries as the power supply at room temperature, the solution could be heated up to the desired temperature within 130 seconds, with the standard deviation less than 0.12° C. during the testing period.

Example 2: High Concentration HIV Preparation

200 µL of a human plasma sample containing HIV viral particles at $5 \times 10^5$ copies/mL was mixed with 600 µL of ZR Viral RNA lysis buffer (Zymo Research) and 30 µL of Triton X100, and mixed at room temperature in an Eppendorf tube to form a lysed sample. Next, the solution was transferred to the sample well in the rotational device. 500 µL of Viral RNA Washing Buffer (containing 80% ethanol, Zymo Research) and 50 µL of Elution Solution (water) were preloaded in designated wells on the device. The cap was applied, and then the device was rotated to the designed positions by holding the top grip and rotating the bottom disk. With rotation, additional positive air pressure was applied by pulling the cap down and compressing the air in the air chamber. The filter layer was rotated 80 degree to the lysis position, additional 114 degree to washing position and additional 102 degrees to elution position Approximately 6 psi positive air pressure was generated at each position. Lysed solution, washing solution, and elution solution were sequentially pushed through the separation material. Each step took approximately 1-2 minutes at room temperature. After each solution passed through the separation material, air (positive pressure in the chamber) was pushed through the separation material as well to dry the filter and minimize the dead volume. Elution solution containing the target nucleic acid was collected at a well in the bottom layer.

Figure 10:
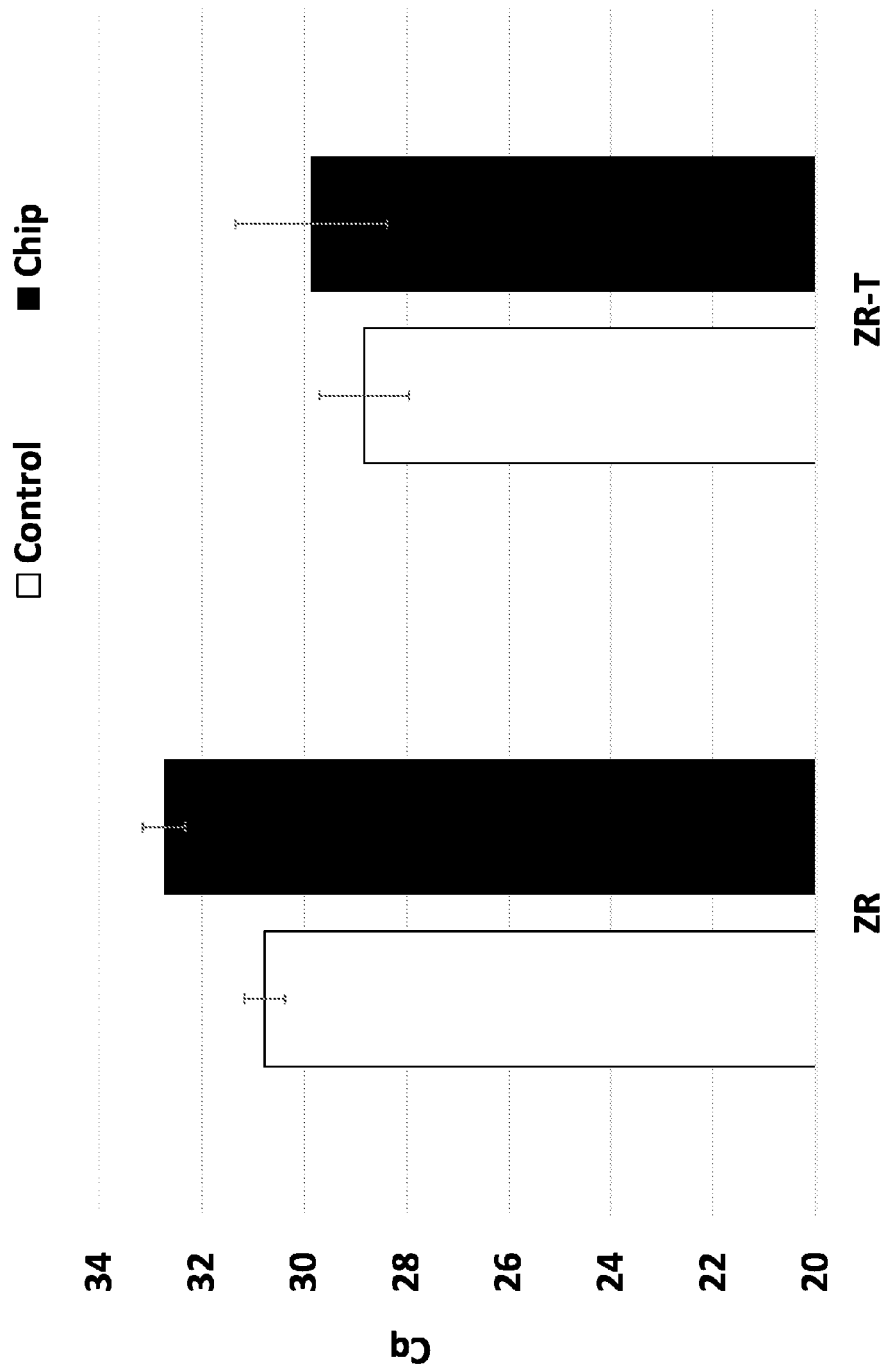
FIG. 10 shows exemplary results from HIV RNA purification and quantification.

Control experiments were performed in parallel following the manufacturer's Zymo Research's standard protocol (Viral RNA) and the optimized protocol (with additional 5% Triton X100) by using centrifugation. Real-time qPCR was used to quantify the concentration of target nucleic acid. The result from experiments (n≥2) for ZR viral RNA protocol on device was 32.74±0.42 Cq (quantitation cycle), compared to 30.77±0.40 Cq for the ZR viral RNA protocol on bench. The result for the ZR viral RNA with Triton X100 protocol (ZR-T) was 29.86±1.48 Cq, compared to 28.86±0.88 Cq for the bench control experiment (see, e.g., FIG. 10).

Example 3: Low Concentration HIV Preparation

Performance of the sample preparation device was further validated with plasma having a low concentration of HIV viral particles. Carrier RNA (Roche) was added to the sample (ZR-T-C), since it has been demonstrated that carrier RNA can improve performance at low concentrations of target molecules. The wells in the sample preparation devices were coated with 1 mg/mL BSA for at least 10 min to further reduce the non-specific adsorption of target molecules.

200 µL of plasma containing viral particles at concentration of $5\times10^3$ copies/mL was mixed with 600 µL of Viral RNA Lysis Buffer (Zymo Research), 30 µL of Triton X100, and 1.5 µL of carrier RNA (5 mg/mL). The solutions were mixed at room temperature in an Eppendorf tube to form a lysed sample. Then, the lysed sample was transferred into a sample well in the rotational device. 500 µL of Viral Wash Buffer (Zymo Research, containing 80% ethanol) and 50 µL of Elution Solution (water) were preloaded into the designated wells on the device. Control experiments were performed at bench with centrifugation protocols. The device was operated as described in the preceding example.

Figure 11:
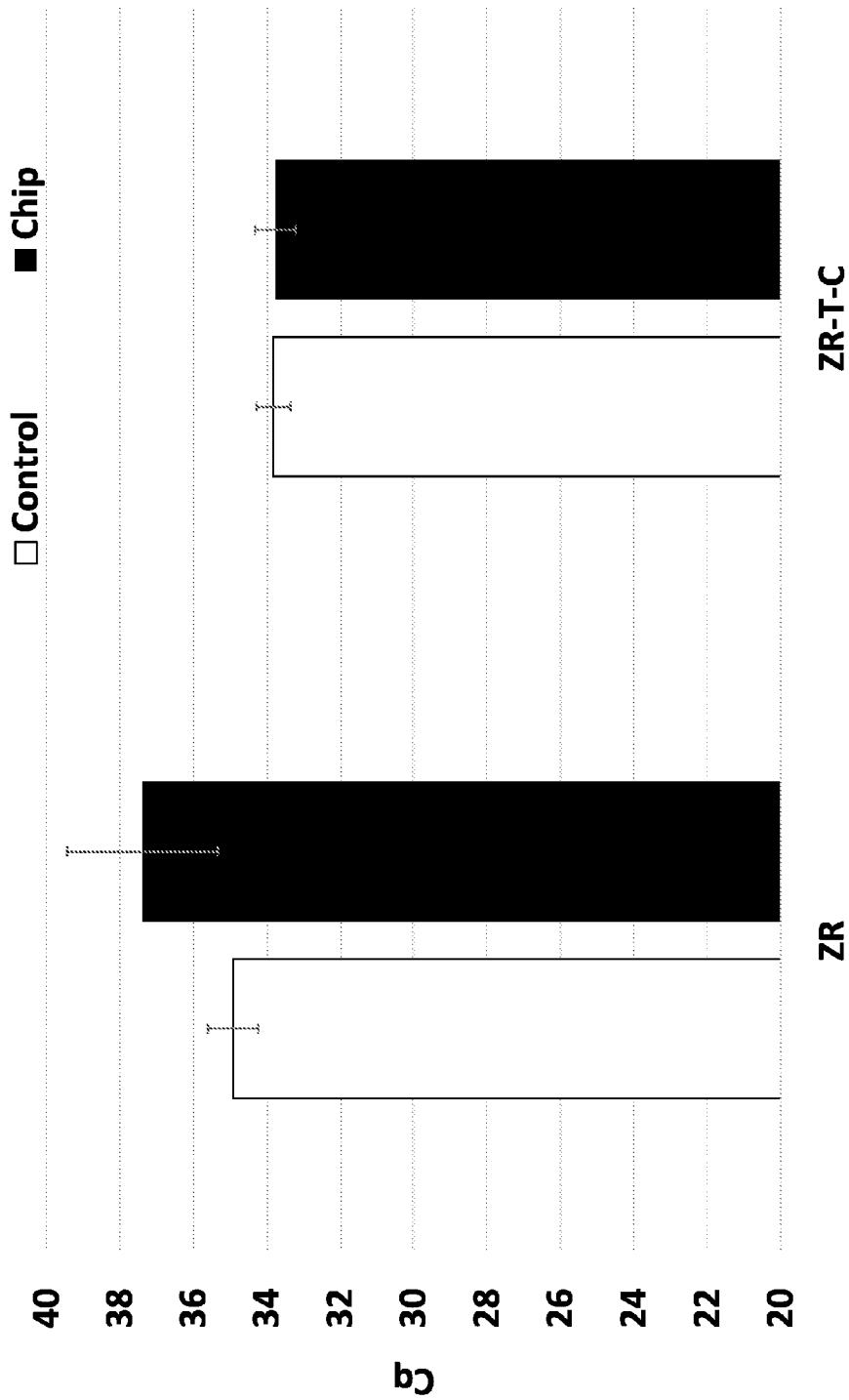
FIG. 11 shows exemplary results from HIV RNA purification and quantification.

Control experiments were performed in parallel following the Zymo Research Viral RNA kit's standard protocol and the optimized protocol (with additional 5% Triton X100) by using centrifugation. The result for the ZR viral RNA protocol (ZR) on the device was 37.39±2.05 Cq, compared to 34.93±0.69 Cq for the bench control (n≥2). The result for optimized protocol with Triton X100 and carrier RNA (ZR-T-C) on the device was 33.77±0.55 Cq, compared to 33.83±0.47 Cq for the bench control (n≥2) (see, e.g., FIG. 11). The results indicate that addition of nonionic surfactants, such as Triton X100, and carrier RNA can improve the performance of HIV viral RNA extraction from plasma at the low concentration of $5\times10^3$ copies/mL.

Example 4: 0.5 mL Sample Preparation Device

Figure 5:
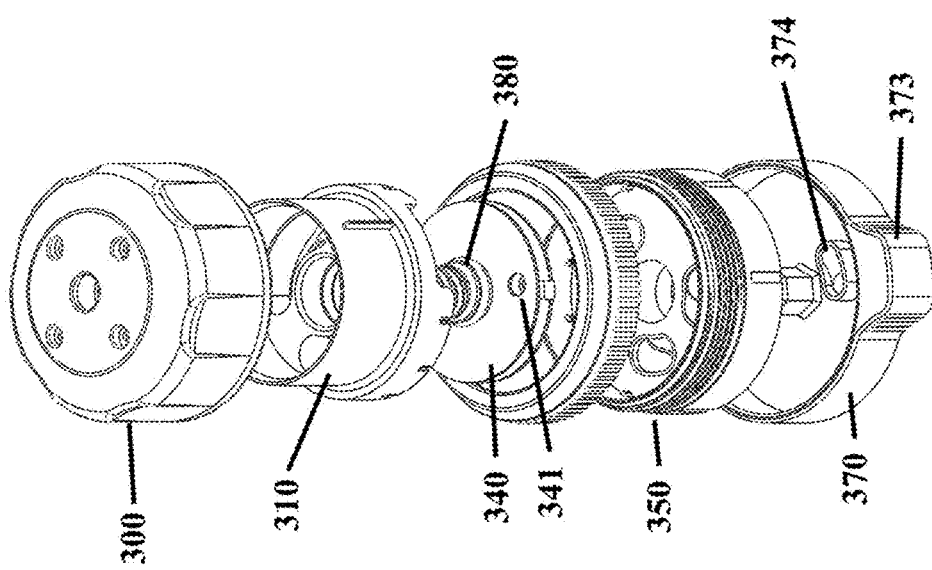
FIG. 5 shows an exemplary exploded three-quarters view schematic of a 0.5 mL device.
Figure 6:
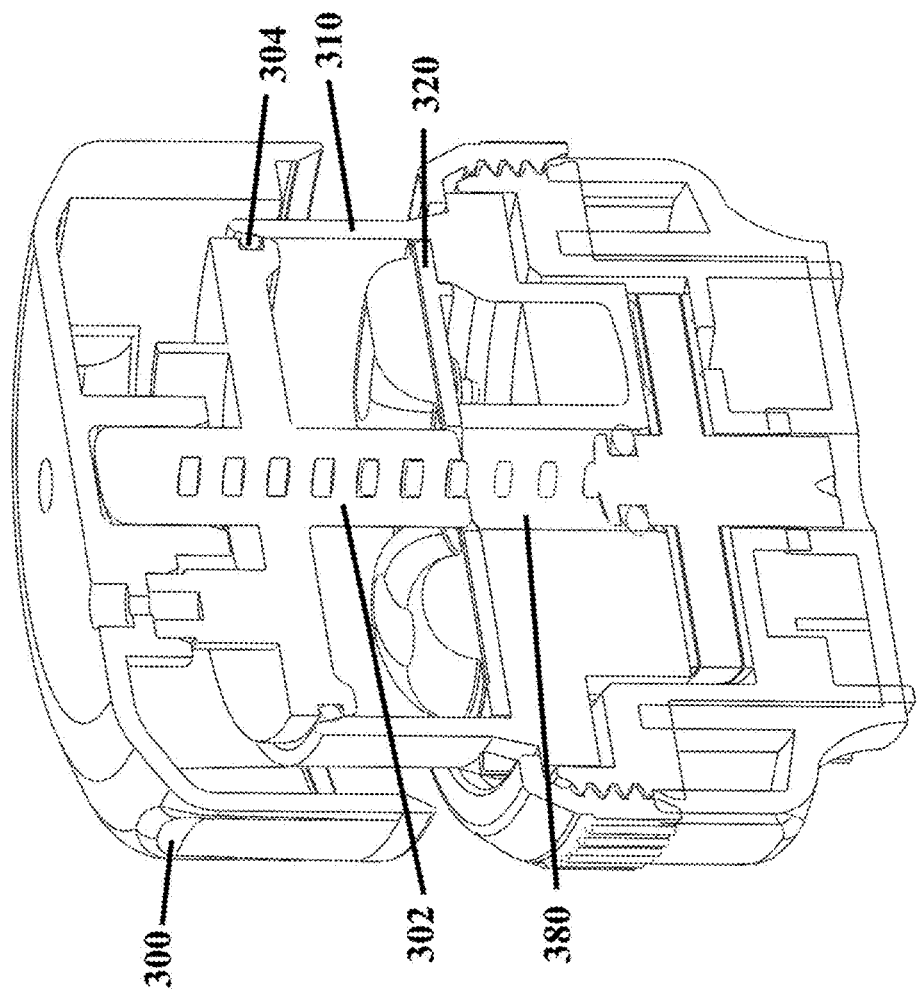
FIG. 6 shows an exemplary cross-section view schematic of the device previously illustrated in FIG. 3.
Figure 7:
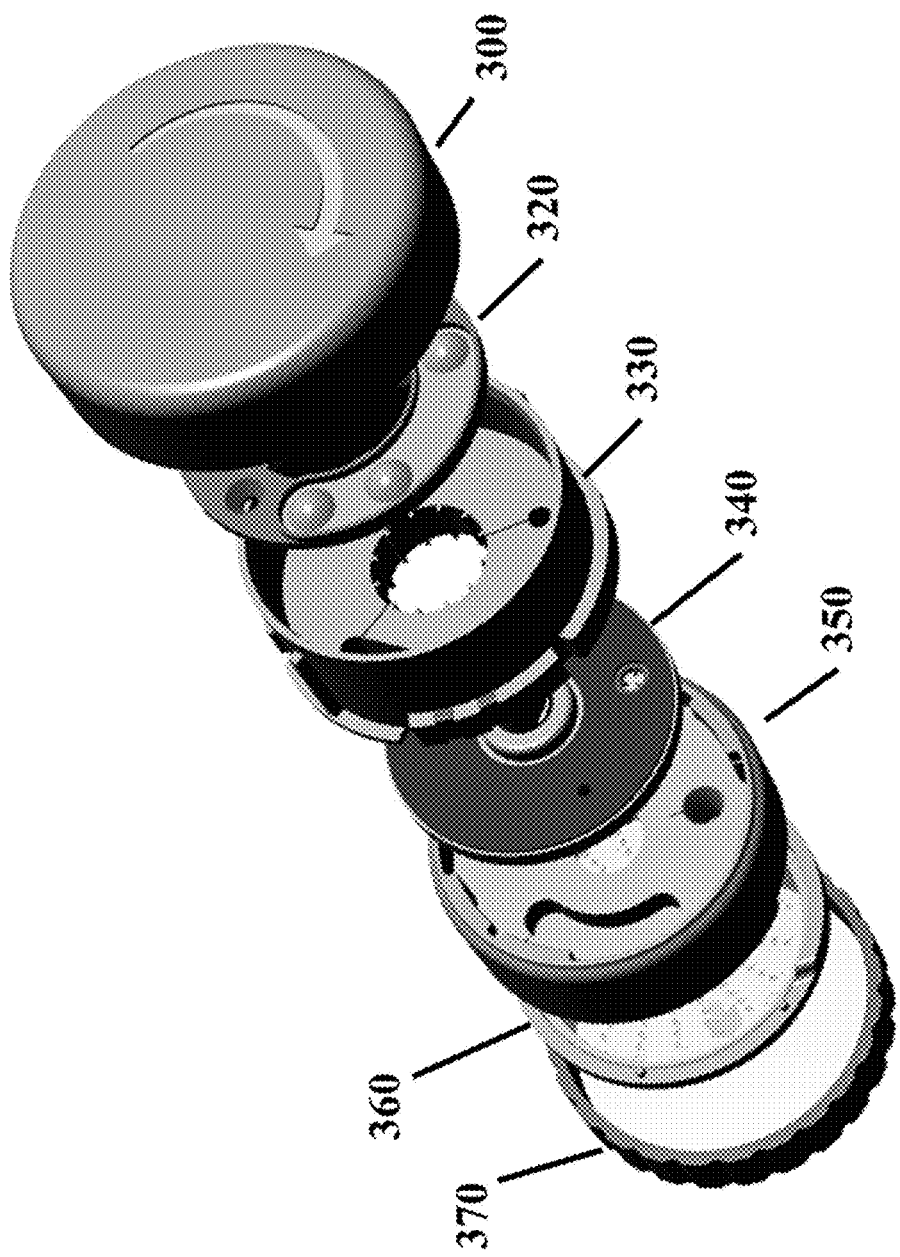
FIG. 7 shows an exemplary exploded view schematic of a device comprising a pressure cap and a plurality of coaxially arranged layers, including an analytic layer.
Figure 8A:
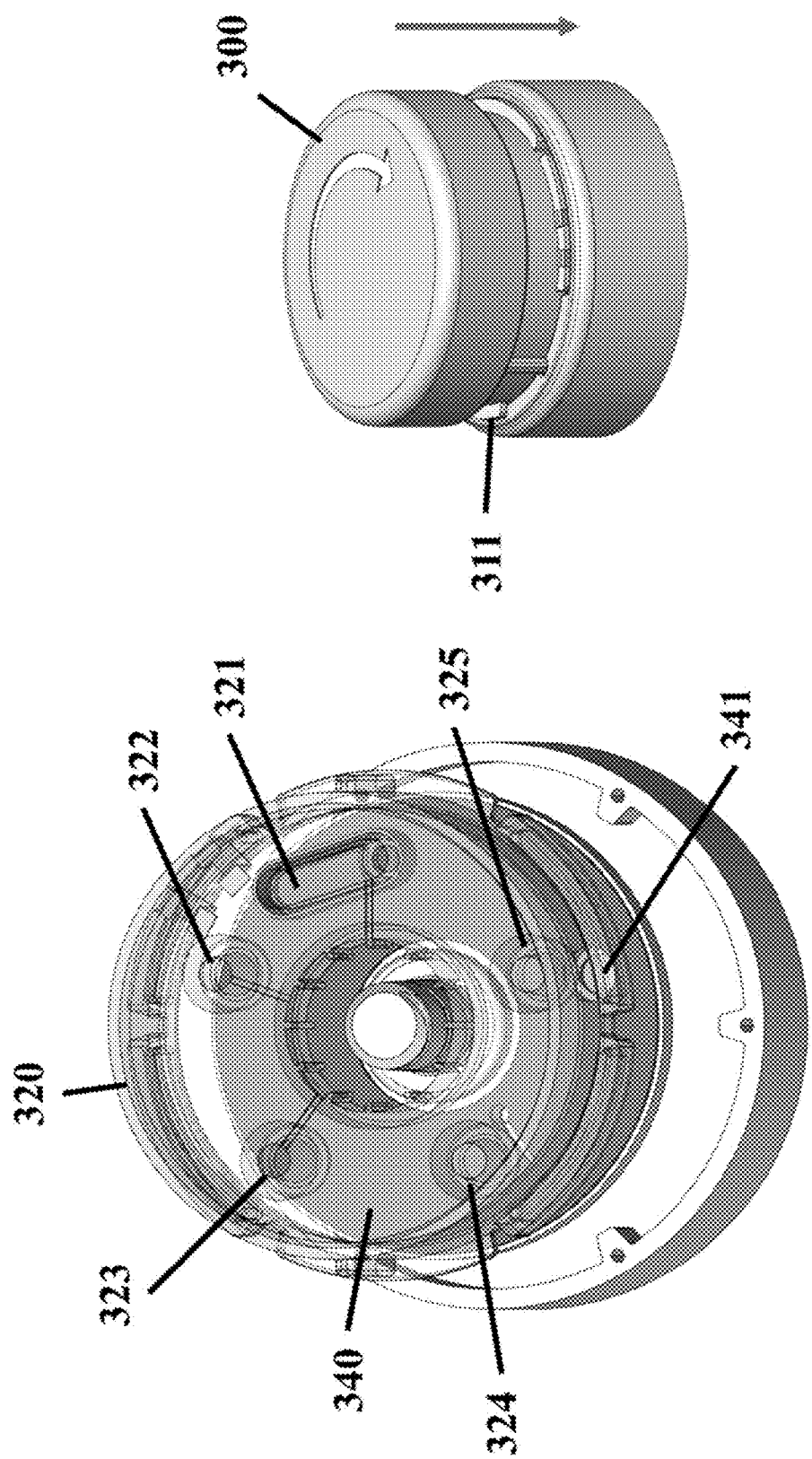
FIG. 8A shows an exemplary schematic of a sample preparation device in a first position.
Figure 8B:
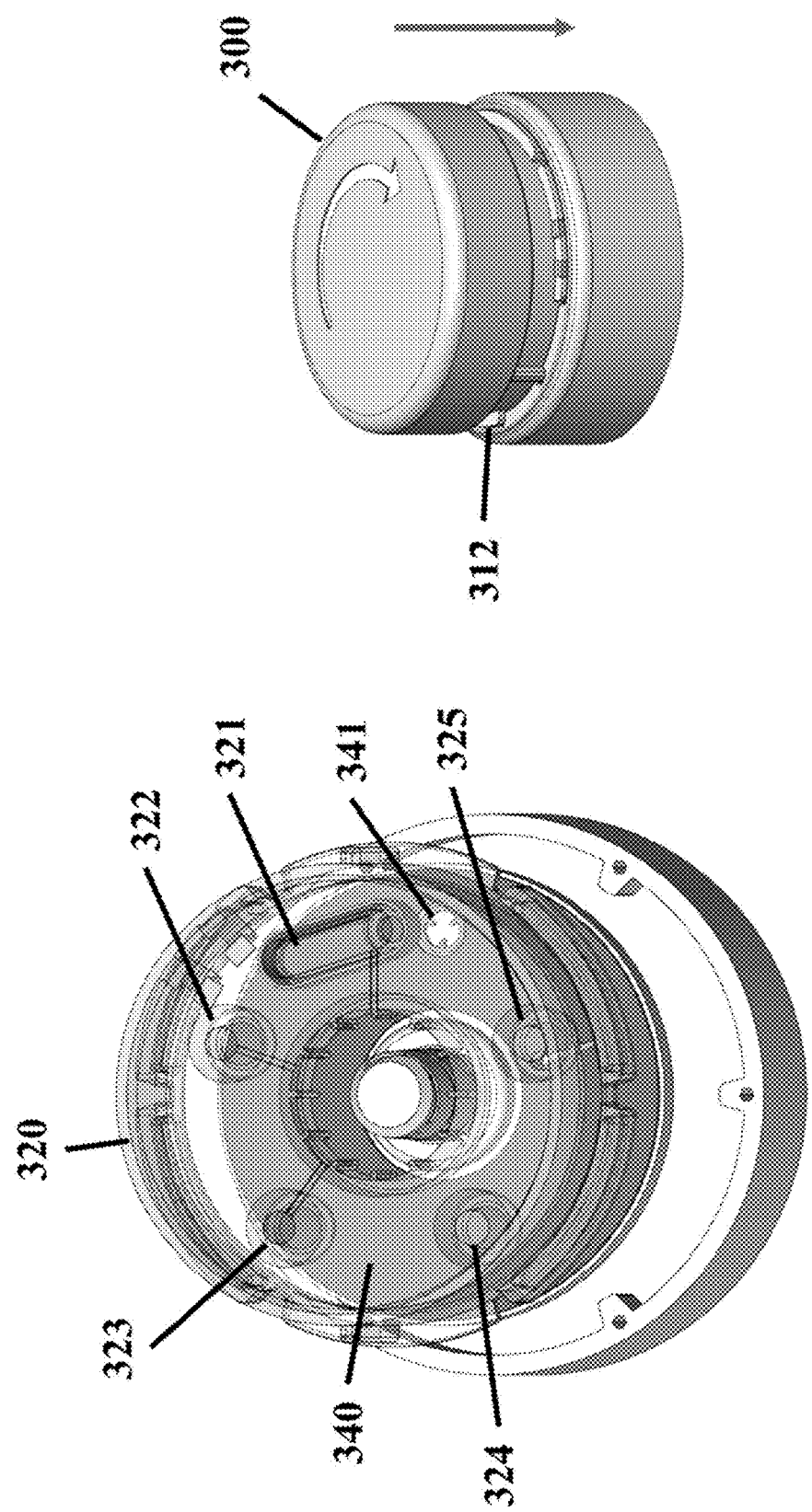
FIG. 8B shows an exemplary schematic of a sample preparation device in a second position.
Figure 8C:
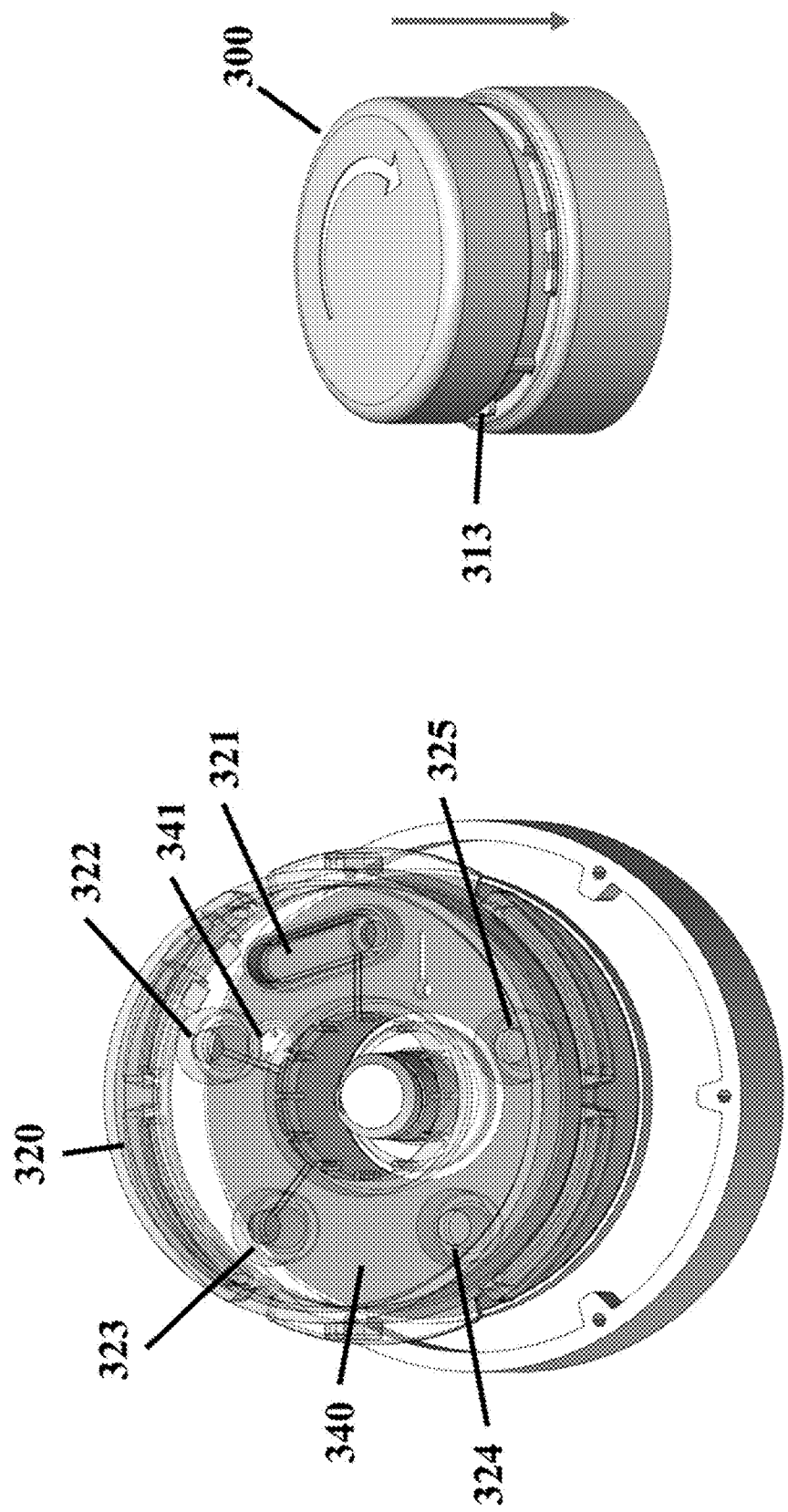
FIG. 8C shows an exemplary schematic of a sample preparation device in a third position.
Figure 8D:
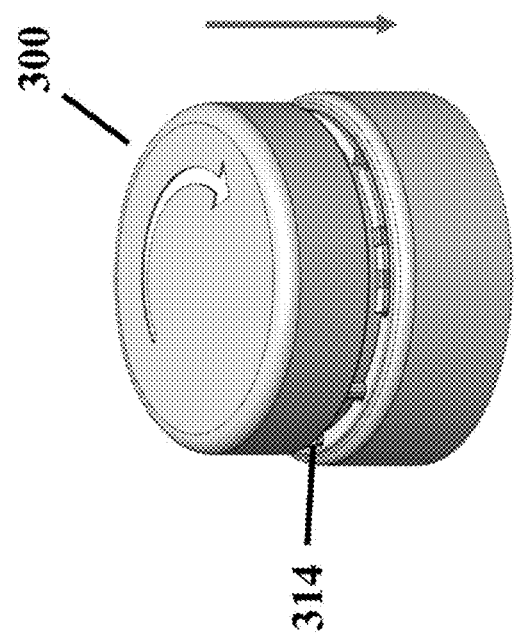
FIG. 8D shows an exemplary schematic of a sample preparation device in a fourth position.
Figure 8D:
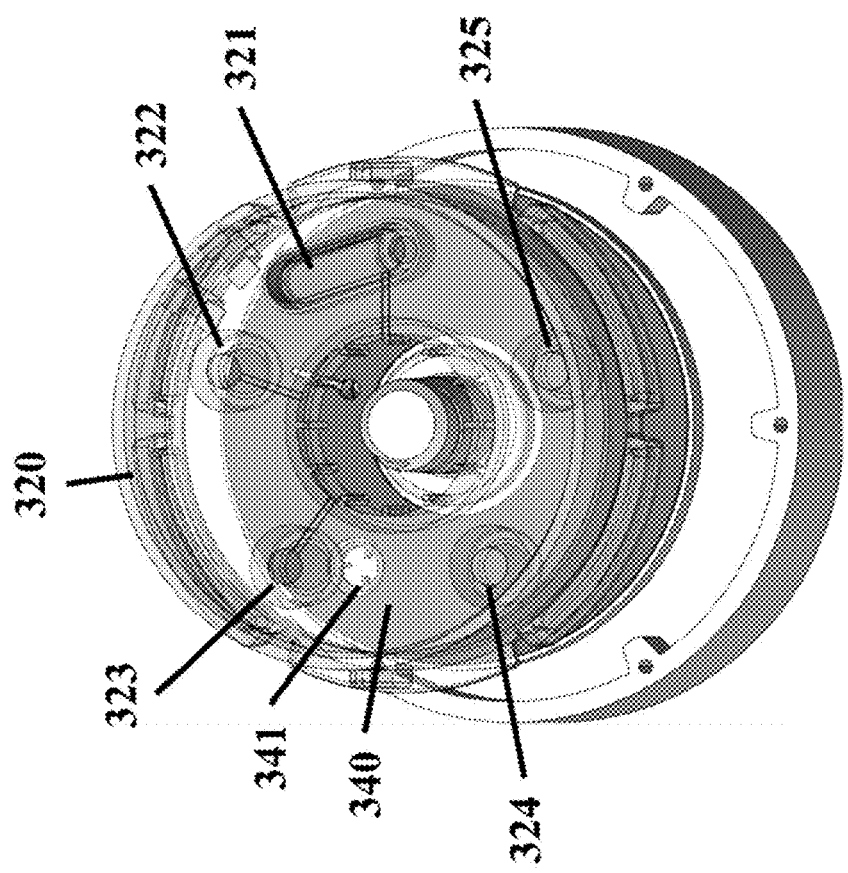

A device that is capable of performing nucleic acid sample preparation with 0.5 mL sample was designed and fabricated using 3D printing (see, e.g., FIG. 5). The device can process: 1) 0.5 mL sample, such as urine or plasma, with up to 1.5 mL lysis buffer; 2) 600 µL of washing buffer; 3) 50 to 100 µL elution buffer. When the purified nucleic acid is eluted in 50 µL elution buffer, it concentrates nucleic acids up to 10-fold from the 0.5 mL input sample.

Example 5: Influenza RNA Extraction

An influenza A virus culture (PR8 strain) and primers for real time qPCR were obtained. QIAamp viral RNA mini kit (Qiagen) was used as a standard control for viral RNA sample preparation. A device, as described in Example 4 above, was preloaded with 600 µL of ZR Viral Lysis buffer, 500 µl of Viral Wash Buffer and 100 µL of water from a viral RNA kit (Zymo Research). The performance of the sample preparation on the device was validated with 200 µL of PBS containing 0.2% BSA and PR8 virus at concentration of $1\times10^4$ pfu/mL and 10 pfu/mL.

Figure 12:
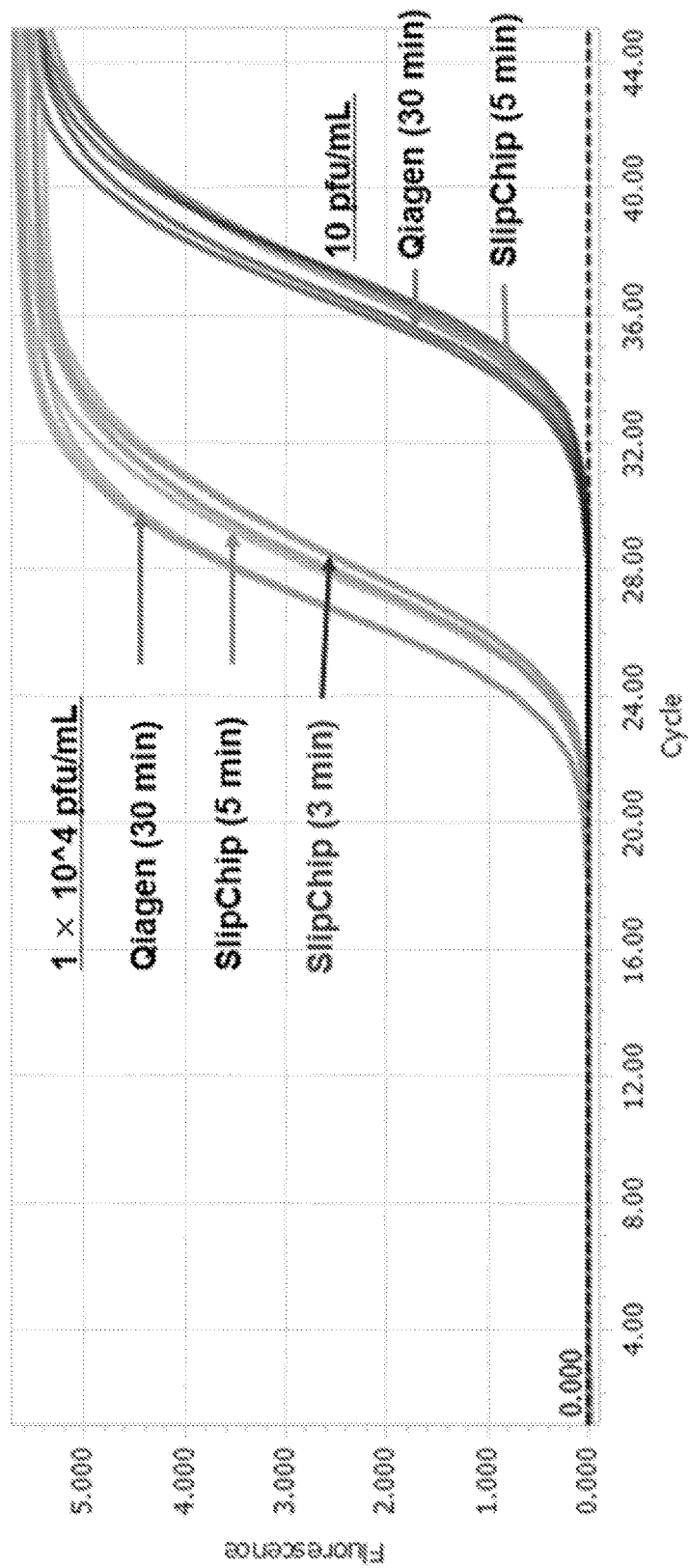
FIG. 12 shows exemplary results from influenza RNA purification and quantification.

The quantification of viral RNA was performed using real time qPCR. Preliminary results indicated that the sample preparation device can perform influenza viral RNA sample preparation as quickly as 3 minutes (see, e.g., FIG. 12).

Example 6: Bacterial RNA Extraction

Extraction and purification of bacterial nucleic acids was evaluated with 1×PBS buffer containing *C. trachomatis* was validated at 20, 50, and 500 copies/mL (copies/mL) (corresponding to 10, 25, and 250 copies/assay). 0.5 mL of PBS buffer spiked with *C. trachomatis* was mixed with 1 mL of lysis buffer (Zymo viral RNA kit). A washing buffer (Zymo viral RNA kit) of 0.8 mL was used to purify the nucleic acid and remove inhibitors. The purified nucleic acid was eluted in 100 µL of water and the performance was quantified using Roche lightcycler real time qPCR. A non-infectious *C. trachomatis* sample (NATtrol™) with a known concentration was purchased from ZeptoMetrix Corporation. The set of primers was designed for 16S gene for *C. trachomatis*. The assay was performed at least three times at each concentration, and 16S nucleic acids were detected in all three experiments at 250 copies/assay, in all five experiments at 25 copies/assay, and in four of the five experiments at 10 copies/assay. Amplification was not observed in the negative control, which did not contain target bacterial nucleic acids.

Separately, bacterial nucleic acids from 0.5 mL human urine samples (Lee Biosolutions) containing organisms of *C. trachomatis* were purified using the 0.5 mL device described above. Viral RNA wash buffer (0.8 mL, containing 80% ethanol, Zymo Research), and Elution Solution (0.1 mL water) were preloaded in the device before experiments. Urine sample (0.5 mL) was mixed with ZR Viral RNA lysis buffer (1 mL, Zymo Research) in a tube under room temperature and then transferred to the sample well. Lysed sample, washing solution, and elution solution were pushed through the sample preparation matrix sequentially by manually rotating the device. The purified nucleic acid was eluted in 100 µL of water, which will concentrate the target nucleic acid five times from 500 µL of input sample. The purified nucleic acid was quantified by using Roche Light-Cycler real time qPCR with primers designed for 16S gene for *C. trachomatis*.

The experiment was repeated four times with 0.5 mL human urine samples containing *C. trachomatis* Serovar D (NATtrol™ *Chlamydia trachomatis* D-UW3 External Run Controls, ZeptoMetrix Corporation) at the concentrations of 20, 50 and 500 copies/mL (copies/mL). 4 out of 4 for 250 copies/assay, 4 out of 4 for 25 copies/assay, and 4 out of 4 for 10 copies/assay were detected. The threshold for detection was Cq<40. No amplification was detected for the negative control experiments, which nucleic acids were extracted from urine samples known to be negative for *C. trachomatis*.

Nucleic acid purification using the 0.5 mL device was confirmed using a different source of chlamydial infected controls, 0.5 mL human urine samples containing *C. trachomatis* acquired from College of American Pathologists (CAP). The CAP samples are commonly used for proficiency testing for different laboratories and instruments. The CAP urine sample was diluted 1:9 (v/v) with negative human urine. The workflow is the same as previously described for urine sample containing NATtrol™ control samples. Three out of three CAP positive samples were detected, while no amplification was observed for negative control experiments.

While benchtop lysis was convenient for initial testing of the device, an on-device lysis protocol and off-device lysis protocol have been compared for sample preparation of bacterial nucleic acid from 0.5 mL urine sample containing CAP samples, diluted 1:9 (v/v). For the on-device lysis protocol, 1 mL of ZR Viral lysis buffer (Zymo Research), 0.8 mL of Viral RNA washing buffer (Zymo Research), and 0.1 mL of elution buffer (water) were preloaded in the device before experiments; 0.5 mL urine sample was introduced in the sample well and mixed with lysis buffer by pipetting. Lysed sample, washing buffer, and elution buffer were pushed through the sample preparation matrix sequentially by manually rotating the device. The entire workflow can be achieved within 5 minutes. Roche real time qPCR has been used to quantify the performance of on-device lysis protocol and off-device lysis protocol. The student t test suggested that there was no significant difference between on-device lysis protocol and off-device lysis protocol (p>0.4).

Example 7: Automated Sample Preparation

A base station was constructed by inexpensive, off-shelf components: a modified servo motor, an encoder with resolution of 1 degree, a 6 V rechargeable battery pack, a main board and a motor driver from Arduino, and a simple control panel with single touch button for user friendly interface. The battery allows at least ten complete runs with a single charge. The center drive will engage with the filter layer of the sample preparation SlipChip device to complete the nucleic acid sample preparation protocol. Three position slots will engage with the locking structure on the base layer of SlipChip device, and hold the device in correct position during operation (see, e.g., FIG. 3D and FIG. 3E).

The base station enables "one-touch" operation for nucleic acid sample preparation on the SlipChip device. The workflow can be accomplished as following (reagents were preloaded to the device before experiments): 1) User introduces 0.5 mL liquid sample to the sample well; 2) User closes the device cap and places the device on the base station; 3) User touches the "start" button. The base station is programmed to finish the workflow in 2 min and 40 sec: first rotate the device for 130 degrees to lysis position and hold for 1 min, then rotate 80 degrees to washing position and hold for 1 min, and lastly rotate 93 degrees to elution position and hold for 30 sec. Elution can be recovered from the base layer for further analysis.

To demonstrate the feasibility of automated sample preparation, the performance of the 0.5 mL sample preparation device was operated by the base station with a urine sample containing NATtrol™ C. trachomatis. 0.5 mL urine was used as the input sample volume in order to extend the limit of detection, and samples containing NATtrol™ C. tracho-matis at 10, 25, 250 copies per assay were tested on device. Viral RNA wash buffer (0.8 mL, Zymo Research) and elution solution (0.1 mL water) were preloaded in the devices before experiments. Urine sample was mixed with 1 mL of ZR Viral RNA lysis buffer (Zymo Research) off-device before transferring into the sample well in the device. The sample preparation device was then placed on the base station, and the user pushed the "start" button to initiate the protocol. The base station automatically manipulated the device: sequentially rotating the device to the correct positions and maintaining the device for 1 min at lysis position, 1 min at washing position, and 30 sec at elution position. Purified bacterial RNA was recovered from the base layer of the device.

Three runs were performed for each concentration of NATtrol™ C. trachomatis, and the base station operated the sample preparation SlipChip device successfully for all 9 runs with a single charge of the battery pack. The concentration of purified C. trachomatis RNA was quantified by using Roche lightcycler real time qPCR. 2 out of 3 for 10 copies/assay, 3 out of 3 for 25 copies/assay (Cq value 35.6±0.4), 3 out of 3 for 250 copies/assay (Cq value 30.4±0.2) were detected. Three negative control experiments with negative human urine samples were also tested on the device, and no amplification was observed.

Example 8: Pressurization

The reproducibility of internal pressure generated in the devices at each step was tested on the 0.5 mL sample size device (see Example 4) and the device was operated by using the base station (see Example 7). Each device was preloaded with 1.5 mL of 20% glycerol in water solution in the sample well, 0.8 mL of 70% ethanol in the washing well, and 0.1 mL of elution buffer (water) in the elution well. Then the device was placed on the base station, and the user pushed the "start" button once to start the workflow sequence. Devices were connected to a pressure gage to record the pressure and voltage was also recorded at the start to show that the station completed all 10 runs with a single battery charge. Three devices were evaluated, and each device was tested with three independent runs (see Table 1). The results indicate reproducible pressure for single device with multiple runs, also similar pressure performance among different devices.

TABLE 1

| Device | Run | Start Pressure (psi) | Lysis Pressure (psi) | Wash Pressure (psi) | Elution Pressure (psi) | Eluate Volume (μL) | Lysis Dead Volume (μL) | Start Voltage (V) |
|---|---|---|---|---|---|---|---|---|
| A | 1 | 3.75 | 8 | 8 | 2.75 | 88 | 34 | 6.32 |
| A | 2 | 3.82 | 8.1 | 7.8 | 2.7 | 81 | 42 | 6.26 |
| A | 3 | 3.77 | 8.1 | 7.5 | 2.75 | 80 | 52 | 6.25 |
| B | 1 | 4.07 | 8.2 | 6 | 2.75 | 80 | 41 | 6.23 |
| B | 2 | 3.98 | 8.3 | 8 | 2.7 | 84 | 30 | 6.23 |
| B | 3 | 4.06 | 8.5 | 8.6 | 2.7 | 81 | 34 | 6.21 |
| B | 4 | 4.04 | 8.4 | 7.2 | 2.65 | 83 | 46 | 6.17 |
| C | 1 | 4.5 | 8.8 | 6.75 | 2.6 | 82 | 33 | 6.2 |
| C | 2 | 4.33 | 8.7 | 7.7 | 2.7 | 76 | 35 | 6.2 |
| C | 3 | 4.23 | 8.8 | 7.6 | 2.7 | 78 | 38 | 6.19 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sample preparation module comprising:
a housing having an interior surface;
a central shaft comprising a threaded section;
a pressure cap comprising:
   a gasket engaged with the interior surface of the housing to create an airtight seal;
   a central column extending centrally from the inner surface of the pressure cap, wherein the central column comprises threads configured to engage the threaded section of the central shaft such that rotation of the central shaft relative to the central column results in movement of said pressure cap linearly along the length of said central shaft;
a plurality of coaxially arranged layers engaged with the central shaft, at least one being a rotor and one being a stator, said coaxially arranged layers having complementary facing surfaces assembled in a frictional, sealed engagement, each layer having at least one passageway with an upstream entry and a downstream outlet capable for successive selective placement in communication to establish plural dedicated flow paths within the assembly, wherein the central shaft extends through the plurality of coaxially arranged layers, and wherein a first coaxially arranged layer engages with the interior surface of the housing to create an airtight seal; and
an airtight compartment formed by the interior surface of the housing engaged in said airtight seal with the gasket of the pressure cap and the interior surface of the housing engaged in the airtight seal with the first coaxially arranged layer,
wherein rotation of the central column relative to the central shaft slidably moves the gasket of the pressure cap or the first coaxially arranged layer along the interior surface of the housing such that the compartment is compressed, thereby generating pressure against the upstream surface of the first coaxially arranged layer, and
wherein rotation of said rotor around said central shaft selectively connects passageways of different coaxial layers thereby serially forming and disrupting a plurality of fluid paths.

2. The sample preparation module of claim 1, wherein the rotor is engaged directly or indirectly with the central shaft and the stator is engaged directly or indirectly with the housing.

3. The sample preparation module of claim 1, wherein the stator is engaged directly or indirectly with the central shaft and the rotor is engaged directly or indirectly with the housing.

4. The sample preparation module of claim 1, wherein the central shaft engages with a drive.

5. The sample preparation module of claim 4, wherein the coaxially arranged layer most proximal to the drive is transparent.

6. The sample preparation module of claim 1, wherein the pressure cap further comprises a key or keyseat that engages with a complementary keyseat or key in the housing thereby inhibiting rotation of the pressure cap relative to the housing.

7. The sample preparation device of claim 1, wherein the pressure cap further comprises a manual grip.

8. The sample preparation module of claim 1, wherein the threads of the central column have a different pitch than the threaded section of the central shaft.

9. The sample preparation module of claim 1, wherein the threaded section of the central shaft is externally threaded and the central column of the pressure cap is internally threaded.

10. The sample preparation module of claim 1, wherein the threaded section of the central shaft is internally threaded and the central column of the pressure cap is externally threaded.

11. The sample preparation module of claim 1, wherein the central shaft comprises a plurality of linked sections, each section engaged with adjacent sections.

12. The sample preparation module of claim 1, wherein the housing is permanently affixed to a coaxially arranged layer.

13. The sample preparation module of claim 1, wherein the housing is comprised of two or more segments that when assembled form airtight junctions.

14. The sample preparation module of claim 13, wherein each of the two or more segments of the housing are permanently affixed to a coaxially arranged layer.

15. The sample preparation device of claim 1, wherein the coaxially arranged layers comprise a reagent layer, a separation layer, and a receiving layer.

16. The sample preparation module of claim 15, wherein the reagent layer receives a sample in a first fluid path that is open to the upstream and downstream surfaces.

17. The sample preparation module of claim 16, wherein the reagent layer comprises a second fluid path that is open to the upstream and downstream surfaces.

18. The sample preparation module of claim 15, wherein the separation layer comprises a separation material occluding the at least one passageway between the upstream and downstream surfaces, said separation material capable of reversibly binding a molecule of interest.

19. The sample preparation module of claim 15, further comprising an analytic layer.

20. The sample preparation module of claim 19, wherein the analytic layer comprises a microfluidic device.

21. The sample preparation module of claim 1, wherein at least one coaxially arranged layer comprises a waste chamber, said waste chamber being a dead end path open only to the upstream surface of the layer.

22. The sample preparation module of claim 1, further comprising a re-sealable sample inlet.

23. A method of isolating a molecule of interest from a sample, the method comprising:
   a) providing a device comprising a pressure cap, a central shaft, and a plurality of coaxially arranged layers, including a reagent layer, a separation layer and a receiving layer;
   b) loading the reagent layer with a lysis solution, a wash solution and an elution solution, each solution occupying a separate passageway having an upstream entry and downstream outlet, wherein each of the downstream outlets of the passageways is occluded in a first position of the device;
   c) combining a sample with the lysis solution in the reagent layer to form a lysed mixture;
   d) rotating the central shaft to a second position, thereby 1) rotating the reagent layer relative to the separation layer to align the outlet of the passageway holding the lysed mixture with the upstream entry of a passageway in the separation layer, said passageway in the separation layer being occluded by a separation material capable of binding the molecule of interest; and 2) moving the pressure cap toward the plurality of coaxially arranged layers, thereby applying positive pressure to the lysed mixture and forcing the lysed mixture onto and through the separation material;

e) rotating the central shaft to a third position, thereby
  1) rotating the reagent layer relative to the separation layer to align the outlet of the passageway holding the wash solution with the upstream entry of the passageway in the separation layer occluded by the separation material; and
  2) moving the pressure cap further toward the plurality of coaxially arranged layers, thereby applying additional positive pressure to force the wash solution through the separation material; and f) rotating the central shaft to a fourth position, thereby
  1) rotating the reagent layer relative to the separation layer to align the outlet of the passageway holding the elution solution with the upstream entry of the passageway in the separation layer occluded by the separation material;
  2) rotating the separation layer relative to the receiving layer to align the outlet of the passageway occluded with the separation material with the upstream entry of a first passageway in the receiving layer; and
  3) moving the pressure cap further toward the plurality of coaxially arranged layers, thereby applying additional positive pressure to force the elution solution through the separation material to detach the molecule of interest from the separation material and collect the elution solution and molecule of interest in the passageway of the receiving layer.

24. The method of claim 23, wherein rotating the central shaft to the second position further comprises rotating the separation layer relative to the receiving layer to align the outlet of the passageway occluded with the separation material with the upstream entry of a second passageway in the receiving layer, said second passageway configured to capture waste liquids.

25. The method of claim 24, wherein the waste liquids are captured in an absorbent housed in the second passageway of the receiving layer.

26. The method of claim 23, wherein the plurality of coaxially arranged layers includes an analytic layer and the method further comprises the step of:

g) rotating the central shaft to a fifth position, thereby
  1) rotating the receiving layer relative to the analytic layer to align the outlet of the passageway holding the elution solution and the molecule of interest with the upstream entry of a passageway in the analytic layer; and
  2) moving the pressure cap further toward the plurality of coaxially arranged layers, thereby applying additional positive pressure to force the elution solution and molecule of interest into the passageway of the analytic layer.

27. The method of claim 26, wherein the molecule of interest is a nucleic acid and the analytic layer is configured to amplify the nucleic acid.

28. The method of claim 23, wherein the sample is provided through a re-sealable sample inlet.

29. The method of claim 23, wherein the molecule of interest is a nucleic acid.

30. The sample preparation module of claim 1, wherein the gasket of the pressure cap or the first coaxially arranged layer is slidably engaged with the interior surface of the housing.

31. A sample preparation module comprising:
a housing having an interior surface;
a central shaft comprising a threaded section;
a pressure cap comprising:
  a gasket engaged with the interior surface of the housing to create an airtight seal;
  a central column extending centrally from the inner surface of the pressure cap, wherein the central column comprises threads configured to engage the threaded section of the central shaft such that rotation of the central shaft relative to the central column results in movement of said pressure cap linearly along the length of said central shaft;
a plurality of coaxially arranged layers engaged with the central shaft, at least one being a rotor and one being a stator, said coaxially arranged layers having complementary facing surfaces assembled in a frictional, sealed engagement, each layer having at least one passageway with an upstream entry and a downstream outlet capable for successive selective placement in communication to establish plural dedicated flow paths within the assembly, wherein the central shaft extends through the plurality of coaxially arranged layers, and wherein a first coaxially arranged layer engages with the interior surface of the housing to create an airtight seal; and
an airtight compartment formed by the interior surface of the housing engaged in said airtight seal with the gasket of the pressure cap and the airtight seal with the first coaxially arranged layer,
wherein rotation of the central column relative to the central shaft slidably moves the gasket of the pressure cap or the first coaxially arranged layer along the interior surface of the housing such that the compartment is compressed, thereby generating pressure against the upstream surface of the first coaxially arranged layer, and
wherein rotation of the central shaft relative to the central column simultaneously
  i) slidably moves the pressure cap or the first layer along the interior surface of the housing such that the compartment is compressed, thereby generating pressure against the upstream surface of the first coaxially arranged layer, and
  ii) rotates the rotor relative to the stator to selectively connect passageways of different coaxial layers thereby serially forming and disrupting a plurality of fluid paths.

* * * * *